United States Patent
Nadaoka et al.

(10) Patent No.: US 7,790,439 B2
(45) Date of Patent: Sep. 7, 2010

(54) BIOSENSOR AND MEASUREMENT METHOD

(75) Inventors: Masataka Nadaoka, Iyo (JP); Mie Takahashi, Niihama (JP); Hirotaka Tanaka, Matsuyama (JP); Fumihisa Kitawaki, Kadoma (JP)

(73) Assignee: Panasonic Corporation, Osaka (JP)

( * ) Notice: Subject to any disclaimer, the term of this patent is extended or adjusted under 35 U.S.C. 154(b) by 6 days.

(21) Appl. No.: 10/416,272

(22) PCT Filed: Aug. 9, 2002

(86) PCT No.: PCT/JP02/08163
§ 371 (c)(1),
(2), (4) Date: May 9, 2003

(87) PCT Pub. No.: WO03/014740
PCT Pub. Date: Feb. 20, 2003

(65) Prior Publication Data
US 2004/0029177 A1   Feb. 12, 2004

(30) Foreign Application Priority Data
Aug. 9, 2001 (JP) ............................. 2001-242765

(51) Int. Cl.
*G01N 33/558* (2006.01)
(52) U.S. Cl. .............. 435/287.2; 422/56; 422/58; 435/287.1; 435/287.7; 435/287.8; 435/287.9; 436/514; 436/518; 436/169
(58) Field of Classification Search .......... 422/50, 422/55–57, 61, 60.1, 62–70, 58, 59, 68.1, 422/69; 435/4, 7.1–7.95, 283.1, 287.2, 288.3, 435/288.4, 288.5, 288.7, 287.7, 287.1, 287.8, 435/287.9; 436/43, 44, 161, 162, 514, 518, 436/528, 529, 530, 164, 169
See application file for complete search history.

(56) References Cited

U.S. PATENT DOCUMENTS 4,906,439 A * 3/1990 Grenner ...................... 422/56

(Continued)

FOREIGN PATENT DOCUMENTS

CA    2 216 189    5/1999

(Continued)

*Primary Examiner*—Melanie Yu
(74) *Attorney, Agent, or Firm*—Wenderoth, Lind & Ponack, L.L.P.

(57) ABSTRACT

In a biosensor having a developing layer for developing a sample solution, including a reagent part immobilized to a portion of the developing layer and a marked reagent part which is held in a dry state by a portion of the developing layer, and is dissolvable by developing the sample solution, and qualitatively or quantitatively analyzing an analyte in the sample solution by measuring the amount of the marker reagent bound to the reagent immobilization part; wherein plural reagent immobilization parts exist, and the respective reagent immobilization parts have different affinities for the analyte in the sample solution or the marker reagent, whereby a prozone phenomenon can be detected. Further, a biosensor with a high precision of measurement, which has a wider dynamic range for the concentration of the analyte in the sample solution, can be provided. Thereby, a highly accurate and precise biosensor which can detect a prozone phenomenon even when the range of the concentration of the analyte in the sample solution is wide, and has a wide measurement dynamic range can be provided.

22 Claims, 7 Drawing Sheets

U.S. PATENT DOCUMENTS

| | | | |
|---|---|---|---|
| 4,956,302 A * | 9/1990 | Gordon et al. | 436/161 |
| 5,356,784 A * | 10/1994 | Kauvar | 435/7.9 |
| 5,459,040 A * | 10/1995 | Hammock et al. | 435/7.1 |
| 5,569,608 A * | 10/1996 | Sommer | 436/518 |
| 5,602,040 A * | 2/1997 | May et al. | 436/514 |
| 5,712,170 A * | 1/1998 | Kouvonen et al. | 436/518 |
| 5,846,838 A * | 12/1998 | Chandler | 436/514 |
| 5,856,203 A * | 1/1999 | Robinson et al. | 436/518 |
| 5,948,695 A * | 9/1999 | Douglas et al. | 436/518 |
| 6,121,008 A * | 9/2000 | Fitzpatrick et al. | 435/7.9 |
| 6,183,972 B1 * | 2/2001 | Kuo et al. | 435/7.1 |
| 6,184,042 B1 * | 2/2001 | Neumann et al. | 436/518 |
| 6,210,978 B1 * | 4/2001 | Hatch et al. | 436/530 |
| 6,248,597 B1 * | 6/2001 | Eda et al. | 436/518 |
| 6,338,969 B1 * | 1/2002 | Shareef et al. | 436/518 |
| 6,478,248 B2 * | 11/2002 | Liu | 242/571.4 |
| 6,485,982 B1 * | 11/2002 | Charlton | 436/514 |
| 6,528,323 B1 * | 3/2003 | Thayer et al. | 436/518 |
| 6,534,768 B1 * | 3/2003 | Ciurczak et al. | 250/339.02 |
| 6,656,745 B1 * | 12/2003 | Cole | 436/514 |
| 6,670,115 B1 * | 12/2003 | Zhang | 435/5 |
| 6,673,628 B2 * | 1/2004 | Freitag et al. | 436/514 |
| 6,830,669 B2 * | 12/2004 | Miyazaki et al. | 204/409 |
| 7,008,799 B1 * | 3/2006 | Zimmer et al. | 436/514 |
| 2001/0006821 A1 | 7/2001 | Ching et al. | |

FOREIGN PATENT DOCUMENTS

| | | | |
|---|---|---|---|
| EP | 0 736 771 | | 10/1996 |
| EP | 0 903 584 | | 3/1999 |
| EP | 0 987 551 | | 3/2000 |
| JP | 8-278305 | | 10/1996 |
| JP | 10-185921 | | 7/1998 |
| JP | 11-326325 | | 11/1999 |
| JP | 2000-46831 | | 2/2000 |
| WO | 99/29429 | * | 6/1999 |
| WO | 00/00826 | | 1/2000 |
| WO | 01/40788 | * | 6/2001 |

* cited by examiner

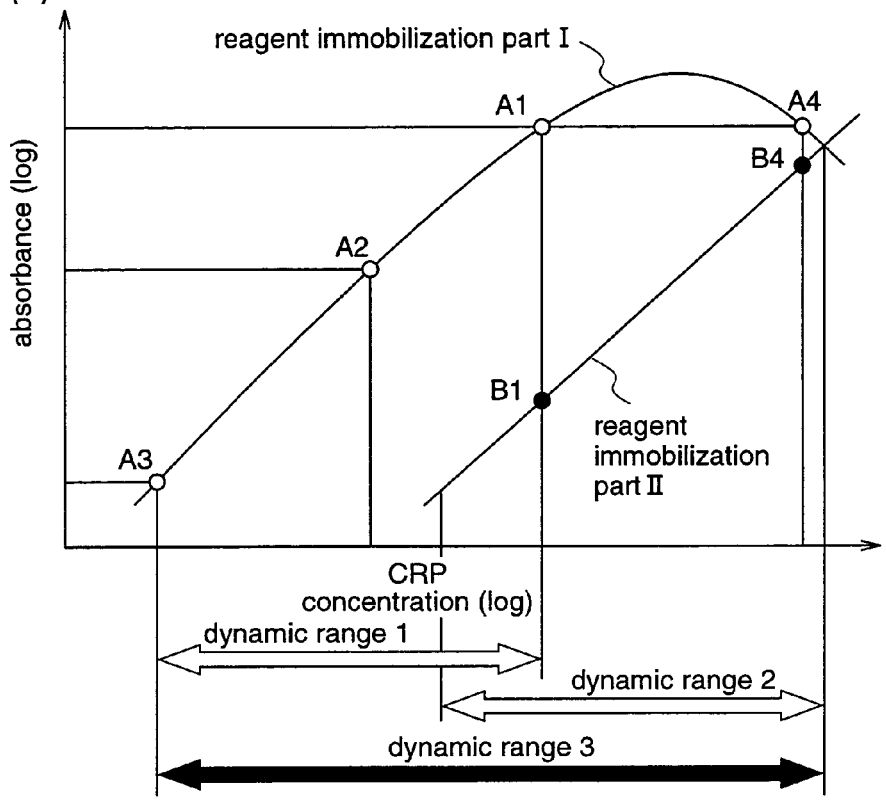
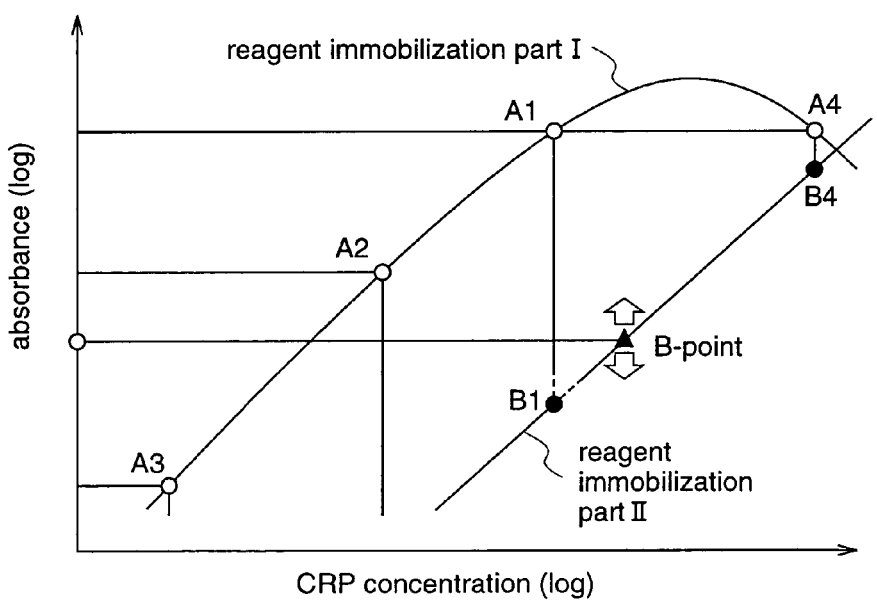

BIOSENSOR AND MEASUREMENT METHOD

This application is a U.S. national stage of International Application No. PCT/JP02/08163 filed Aug. 9, 2002.

TECHNICAL FIELD

The present invention relates to a biosensor and a measurement method and, more particularly, to a biosensor utilizing chromatography and a measurement method using the biosensor.

BACKGROUND ART

Conventionally, there is an immunochromatography sensor as a typical example of a biosensor which is provided with a developing layer for developing a sample solution, includes a reagent part immobilized to a portion of the developing layer and a marked reagent part that is held by a portion of the developing layer in a dry state and is dissolvable by developing the sample solution, and measures the amount of the marker reagent bound to the reagent immobilization part, thereby to qualitatively or quantitatively analyze an analyte in the sample solution.

A general example of an immunochromatography sensor is provided with a sample applying part to which a sample solution is applied, and plural developing layers, and an antibody is immobilized to portions of the developing layers. Further, a marker antibody is held at the upper stream than the antibody immobilization part in a dry state so that it is dissolvable by the sample solution. When a required amount of sample solution is applied to the sample applying part, the sample solution penetrates through the developing layers, whereby measurement is started. A result of measurement is detected by the marker antibody that is bound to the antibody immobilization part. Particles of gold colloid are commonly used as a marker, and the binding to the antibody immobilization part is visually observable due to the particles of gold colloid. Thus, the result of measurement is obtained by visual observation. While sandwich reaction of antigen-antibody reaction is employed as a measurement principle, even when competition reaction is employed as a measurement principle, a result of measurement can be obtained by observing the state of binding of the marker reagent to the antibody immobilization part. In this specification, "immune chromatography" and "immunochromatography" denote the same chromatography, and it is an immunomeasurement method in which complexes of an immobilized reagent and a marker reagent are produced in a reaction layer comprising a wettable porous material, thereby to measure an analyte. That is, it is a measurement system utilizing antigen-antibody reaction. While the conventional immunomeasurement method needs a cleaning operation such as B/F separation, in the immunochromatography method, B/F separation is executed during the process in which the sample solution penetrates through a chromatography carrier as a reaction layer. Usually all reagents are in their dry states, and they are wetted by the sample solution during measurement. While gold colloid and latex are common as markers, magnetic particles, enzymes, and metal colloids other than gold colloid may be used. When the marker is an enzyme or the like, a user operation of adding an enzyme substrate or a reaction stopping agent is included as a measurement operation. Further, amongst the above-mentioned immunochromatography methods, one-step immunochromatography is a measurement method in which measurement is carried out by only a user operation of adding a sample solution. Since the fundamental measurement operation by the user is only application of a sample solution, it is called one-step immunochromatography. Further, although the above-described method requires qualitative judgement by visual observation, when a desired result of measurement is semi-quantitative or when judgement with accuracy higher than that is required, there is employed a method of reading a result of measurement by a transparent mode using an optical reading device, which is disclosed in Japanese Published Patent Application No. Hei.10-274624, or a method of capturing a result of measurement as an image with a camera or the like, and arithmetically processing the image, which is disclosed in Japanese Published Patent Application No. Hei.10-274653.

On the other hand, examples of a sensor device having the function of performing quantitative analyze by itself without requiring a measurement device for directly detecting a signal from the sensor by visual observation, have been disclosed in Japanese Patent No. 3005303, Japanese Published Patent Application No. Hei.7-159398, Japanese Published Patent Application No. Hei.8-278305. These inventions provide a sensor having the function of quantitative analysis by detecting the number of parts to which a marker reagent is bound among plural reagent immobilization parts, a sensor having the function of semi-quantitative analysis by varying the concentration in a reagent immobilization part, and a sensor which can simultaneously measure different target items in plural reagent immobilization areas.

In recent years, POCT (Point-of-Care Tests) is gradually becoming widespread in medical diagnosis scenes. In POCT, especially, a device that can measure an analyte speedily, easily, and precisely is desired. A fundamental principle employed for POCT has convenience that can deal with a wide range of analytes, and it is progressing in various fields not only clinical fields but also food hygiene fields, environmental measurement fields, and the like. On the other hand, although some POCT have quantitativeness for limited target items, most of POCT have only qualitative or semi-quantitative accuracy, and therefore, a technique that can measure an analyte more speedily, easily, and accurately and is applicable to wider fields has been demanded. However, while in the above-described method the analyte is measured by detecting the amount of the marker reagent bound to the reagent immobilization part in the sensor, the binding of the marker reagent to the reagent immobilization part has limitations. First of all, in the case of using sandwich reaction, a measurable antigen concentration area is eventually limited. Especially when it is antigen-antibody reaction, the antigen concentration in the area where the amount of binding linearly increases is about single or double digits. Even when more target antigen exists, it is saturated at a predetermined amount of binding, and the antigen exceeding the saturation level cannot be bound to the reagent immobilization part. When the target antigen further increases, a prozone phenomenon occurs. Therefore, when the concentration of the target antigen is high, previous dilution is needed. In order to perform dilution as well as execute highly precise quantitative analysis, dilution precision is also needed as a matter of course, and a device for dilution is required and, further, a dilution operation is required. Such dilution operation is extremely complicated for unskilled persons having little experience of chemical experiments, and therefore, the user must be selected. Furthermore, when such operational precision is not required, dilution can be carried out with relative ease by using a common pipette or the like. In this case, however, precision cannot be expected. Moreover, since the dilution operation is needed in addition to the measurement operation, extra time is required. Therefore, when speedy measurement in POCT is required, the measurement method using sandwich reaction can be used for only lower-accuracy qualitative analysis or semi-quantitative analysis. Further, a serious problem of the prozone phenomenon resides in that, even when the concentration of the actual analyte in the sample solution is high, a result apparently equivalent to a low concentration is undesirably obtained. For example, in the case of measurement in a clinical test, since a prescription for a patient is selected according to the test result, such prozone phenomenon might cause, in extreme cases, a problem relating to continuation of life. Accordingly, false-negative (FN) due to prozone phenomenon can be a fatal problem for the measurement.

Next, in the case of using competitive reaction, the amount of the marker reagent bound to the reagent immobilization part decreases with an increase in the concentration of the target antigen, and the marker reagent is not bound to the reagent immobilization part when the concentration of the target antigen is higher than a predetermined level. Also in this competitive reaction, when an antibody and an antigen are used as the immobilized reagent components, the target antigen concentration area is eventually limited due to the nature of binding, and a dilution operation is needed when the concentration of the target antigen is high, as in the above-mentioned sandwich reaction. In order to perform dilution as well as highly-precise quantitative analysis, dilution precision is also required as a matter of course, and a device for dilution is required and, furthermore, a dilution operation is required. Such dilution operation is extremely complicated for unskilled persons having little experience of chemical experiments, and therefore, the user must be selected. Furthermore, when such operational precision is not desired, dilution can be carried out with relative ease by using a common pipette or the like. In this case, however, precision cannot be expected. Moreover, since the dilution operation is needed in addition to the measurement operation, extra time is required. Therefore, when speedy measurement in POCT is required, the measurement method using competitive reaction can be used for only lower-accuracy qualitative analysis or semi-quantitative analysis. Further, only analytes having less change in target antigen concentration can be selected. Moreover, in order to measure an analyte having a wide concentration range without performing dilution, plural sensor devices must be used. When plural sensor devices are used, since the concentration of the analyte in the employed sample solution is not known by the operator, the operator must perform measurement twice, resulting in complicated workability and increased costs.

DISCLOSURE OF THE INVENTION

In order to solve the above-described problems, there is provided a biosensor which has a developing layer for developing a sample solution, includes a reagent part immobilized to a portion of the developing layer and a marked reagent part that is held by a portion of the developing layer under a dry state and is dissolvable by developing the sample solution, and measures the amount of the marker reagent bound to the reagent immobilization portion, thereby to qualitatively or quantitatively analyze an analyte in the sample solution; wherein plural reagent immobilization parts exist, and the plural reagent immobilization parts have different affinities for the analyte in the sample solution or the marker reagent. Since the plural reagent immobilization parts are provided and the respective parts have different affinities for the analyte in the sample solution or the marker reagent, a prozone phenomenon can be detected, and furthermore, the dynamic range of the concentration of the analyte in the sample solution can be increased. The "prozone phenomenon" described in this specification indicates, for example, an antigen excess area and a post-zone area in measuring an antigen in an antigen-antibody reaction. When a sandwich reaction system in the above-described immunochromatography sensor is taken as an example, complexes of immobilized reagent, analyte, and marker reagent are generated in the reagent immobilization parts in accordance with the concentration of the analyte in the sample solution, and the amount of the complexes to be formed increases as the concentration of the analyte in the sample solution increases. However, when the concentration of the analyte reaches a predetermined level, the complex formation amount is saturated. When the concentration of the analyte exceeds the level, the complex formation amount decreases. At last, the concentration of the analyte reaches an area where no complex is formed. The phenomenon that occurs in the area where the complex formation amount decreases and the area where no complex is formed at all although the analyte exists at a high concentration, is called "prozone phenomenon". While the prozone phenomenon is described with respect to the sandwich reaction in the immunochromatography sensor having an antigen as an analyte, it is needless to say that this phenomenon also occurs when the analyte is an antibody in a sandwich reaction system which forms complexes in similar manner, or in a reaction system utilizing a binding reaction. Further, the above-described analyte dynamic range means the measurable range of the concentration of the analyte in the test solution. For example, depending on the measurement method, there are cases where the concentration of the original sample solution is measured as it is, or where the measurable range is made wider by dilution or the like. However, the dynamic range described here is a pure measurable range in the case where the sample solution is used as it is, without adding a diluent or the like. The dynamic range will be described taking a perfect dry system immunochromatography sensor as an example. At present, there is an immunology test for pregnancy using urine as a specimen, which is commonly used in clinical scenes or homes. In this case, the user drops urine onto a sensor device to complete an operation relating to measurement, and checking a test result is only left for the user to do. That is, in this case, the range of concentration that is actually measurable when urine is dropped as it is, is called an analyte dynamic range. This is merely an example, and the same can be said of other analytes, samples, and reaction modes.

The present invention is made to solve the above-described problems and has for its object to detect a prozone phenomenon by making the plural reagent immobilization parts have different affinities for the analyte or the marker reagent even when the concentration of the analyte in the sample solution is high. Furthermore, it is another object of the present invention to provide a biosensor which can measure a wider range of concentration of the analyte by making the plural reagent immobilization parts have different affinities, and therefore, can select analytes over a wide range.

According to Claim 1 of the present invention, there is provided a biosensor having a developing layer for developing a sample solution, including a reagent part immobilized to a portion of the developing layer and a marked reagent part which is held in a dry state by a portion of the developing layer, and is dissolvable by developing the sample solution, and qualitatively or quantitatively analyzing an analyte in the sample solution by measuring the amount of the marker reagent bound to the reagent immobilization part; wherein plural reagent immobilization parts exist, and the respective reagent immobilization parts have different affinities for the analyte in the sample solution or the marker reagent. The biosensor is characterized by that plural reagent immobilization parts are provided, and the respective reagents have different affinities for the analyte in the sample solution or the marker reagent.

According to Claim 1 of the present invention, there is provided a biosensor which is a device having a developing layer for developing a sample solution, including a reagent part immobilized to a portion of the developing layer and a marked reagent part which is held in a dry state by a portion of the developing layer, and is dissolvable by developing the sample solution, and having a sample applying part on which the sample solution is applied, the marker reagent part, and the marker immobilization part which are arranged in this order, said biosensor qualitatively or quantitatively analyzing an analyte in the sample solution by measuring the amount of the marker reagent bound to the reagent immobilization part; wherein plural reagent immobilization parts exist, and the respective reagent immobilization parts have different affinities for the analyte in the sample solution or the marker reagent. The biosensor is a device having the sample applying part, the marker reagent part, and the reagent immobilization parts in this order, and further, it is characterized by that plural reagent immobilization parts exist, and the respective reagent immobilization parts have different affinities for the analyte in the sample solution or the marker reagent.

According to Claim 2 of the present invention, in the biosensor as defined in Claim 1, the reagents immobilized to the plural reagent immobilization parts are antibodies, the analyte in the sample solution is an antigen, and an antibody having a higher affinity for the analyte in the sample solution or the marker reagent is immobilized to the reagent immobilization part that is positioned on the upper stream side with respect to the sample solution applying part. In the biosensor as defined in Claim 1, the reagent immobilization parts are antibodies, and the analyte in the sample solution is an antigen, and further, an antibody having a higher affinity for the antigen is provided on a part at the upper stream side in the sample penetrating and developing direction with respect to the sample solution applying part, that is, the antibody is provided on a part which earlier comes in contact with a developing mixture solution which develops while dissolving the marker material after the sample solution is applied to start development.

According to Claim 3 of the present invention, in the biosensor as defined in any of Claims 1 or 2, the reagents in the plural reagent immobilization parts are monoclonal antibodies. In the biosensor as defined in any of Claims 1 or 2, each of the reagents on the plural reagent immobilization parts is a monoclonal antibody.

According to the present invention, in the biosensor, the analyte in the sample solution is quantitatively analyzed by measuring the amount of the marker reagent bound to the plural reagent immobilization parts. In the biosensor as defined in any of Claims 1 to 4, the analyte in the sample solution is measured by measuring the amount of the marker reagent bound to the reagent immobilization parts.

According to the present invention, in the biosensor, a prozone phenomenon is detected by measuring the amount of the marker reagent bound to the plural reagent immobilization parts. In the biosensor, by measuring the marker reagent binding states in the plural reagent immobilization parts, it is detected whether or not the respective parts are prozone areas in the measurement. Although the prozone area has already been described, the prozone area described in this specification indicates, for example, an antigen excess area and a post zone area in measuring an antigen in an antigen-antibody reaction. When a sandwich reaction system in the immunochromatography sensor is taken as an example, complexes of immobilized reagent, analyte, and marker reagent are generated in the reagent immobilization parts in accordance with the concentration of the analyte in the sample solution, and the amount of the complexes to be formed increases as the concentration of the analyte in the sample solution increases. However, when the concentration of the analyte reaches a predetermined level, the complex formation amount is saturated. When the concentration of the analyte is higher than the level, the complex formation amount decreases. When the concentration of the analyte further increases, it reaches an area where no complex is formed. A part which is generally called a zone area or a zone phenomenon, including the area where the complex formation amount decreases and the area where no complex is formed at all although the analyte exists at a high concentration, is called a prozone area. While the sandwich reaction in the immunochromatography sensor is taken as an example, it is needless to say that a prozone area is a phenomenon that also occurs when the analyte is an antibody in a sandwich reaction system which forms complexes in similar manner, or in a reaction system utilizing binding reaction.

According to the present invention, in the biosensor, among the plural reagent immobilization parts, the amount of the marker reagent bound to the reagent immobilization part which is positioned on the uppermost stream side with respect to the sample solution applying part is measured, thereby to measure the analyte in the sample solution; and the amounts of the marker reagent bound to the other reagent immobilization parts are also measured and, on the basis of the results of the respective measurements, the measured value of the amount of the marker reagent bound to the uppermost-steam side reagent immobilization part is subjected to prozone judgement. In the biosensor, the analyte in the sample solution is measured by measuring the amounts of the marker reagent bound to the plural reagent immobilization parts. At this time, in measuring the sample solution, the measurement is carried out using the reagent immobilization part positioned at the uppermost stream side viewed from the sample solution applying part, and the bindings of the marker reagent in the other reagent immobilization parts are subjected to prozone judgement, thereby to judge as to whether the binding of the marker reagent in the uppermost-stream side reagent immobilization part is a prozone area or not.

According to Claim 4 of the present invention, in the biosensor as defined in any of Claims 1 to 3, the plural reagent immobilization parts have different affinities for the analyte in the sample solution or the maker reagent, whereby the respective reagent immobilization parts have different dynamic ranges for measuring the concentration of the analyte in the sample solution. In the biosensor as defined in any of Claims 1 to 3, the plural reagent immobilization parts have different affinities for the analyte in the sample solution or the maker reagent, whereby the respective reagent immobilization parts have different dynamic ranges for measuring the concentration of the analyte in the sample solution. The dynamic range means, as already described above, a pure measurable concentration range of the analyte in the case where the sample solution is used as it is, without adding a diluent or the like. The dynamic range will be described taking a perfect dry system immunochromatography sensor as an example. At present, there is an immunology test for pregnancy using urine as a specimen, which is commonly used in clinical scenes or homes. In this case, the user drops urine onto a sensor device to complete an operation relating to measurement, and checking a test result is only left for the user to do. That is, in this case, the actually measurable range when urine is dropped as it is, is called an analyte dynamic range. This is merely an example, and the same can be said of other analytes, samples, and reaction modes. Further, even when an operation such as dilution is required in the measurement system, a detection sensitivity area for the same sample solution and the same analyte is defined as a dynamic range.

According to the present invention, in the biosensor, the plural reagent immobilization parts have different affinities for the analyte in the same solution or the marker reagent, thereby to increase the dynamic range for measuring the concentration of the analyte in the sample solution. In the biosensor as defined in Claim 8, when the analyte in the sample solution is measured by measuring the amounts of the marker reagent bound to the plural reagent immobilization parts, since the plural reagent immobilization parts have different affinities for the analyte in the same solution or the marker reagent, the respective parts show different responses to the concentration of the analyte in the sample solution, whereby the analyte dynamic range of the sensor device is increased.

According to Claim 5 of the present invention, in the biosensor as defined in any of Claims 1 to 4, the plural reagent immobilization parts recognize the same epitope. In the biosensor as defined in any of Claims 1 to 4, the reagents in the plural reagent immobilization parts recognize the same epitope although they have different affinities for the analyte in the sample solution or the marker reagent. Recognizing the same epitope means that the plural reagent immobilization parts are bound to the same binding site although they have different affinities for the binding site.

According to Claim 6 of the present invention, in the biosensor as defined in any of Claims 1 to 5, the reagent immobilization parts are provided in two positions. In the biosensor as defined in any of Claims 1 to 5, the plural reagent immobilization parts are provided in two positions.

According to Claim 7 of the present invention, in the biosensor as defined in any of Claims 1 to 6, the plural reagent immobilization parts are in contact with each other. In the biosensor as defined in any of Claims 1 to 6, the respective reagent immobilization parts are in contact with each other.

According to Claim 9 of the present invention, in the biosensor as defined in any of Claims 1 to 7, the developing layer employs a lateral flow system, the plural reagent immobilization parts are immobilized in lines along a direction perpendicular to the sample solution developing direction, the line width is 0.5 mm~2.0 mm, and the intervals between the lines of the plural reagent immobilization parts are 1.0 mm or longer. In the biosensor as defined in any of Claims 1 to 7, the developing layer employs a lateral flow system, the plural reagent immobilization parts are immobilized in lines along a direction perpendicular to the sample solution developing direction, the line width is 0.5 mm~2.0 mm, and the intervals between the lines of the respective reagent immobilization parts are 1.0 mm or longer.

According to Claim 9 of the present invention, in the biosensor as defined in any of Claims 1 to 8, all of the reagents including the marker reagent and the immobilized reagents are in their dry states. In the biosensor as defined in any of Claims 1 to 8, all of the reagents including the marker reagent and the immobilized reagents are in dry states. The dry state means the state before measurement is carried out, that is, the state before the reagents are wetted by the sample solution.

According to Claim 10 of the present invention, in the biosensor as defined in any of Claims 1 to 9, the sample solution is urine, saliva, or blood. In the biosensor as defined in any of Claims 1 to 9, the sample solution is urine, saliva, or blood. The blood includes whole blood containing a material component such as blood corpuscle, blood serum excluding a material component, and blood plasma.

According to Claim 11 of the present invention, in the biosensor as defined in any of Claims 1 to 10, the biosensor is used immunochromatography. The biosensor as defined in any of Claims 1 to 10 is used immunochromatography.

According to Claim 12 of the present invention, there is provided a measurement method employing a biosensor as defined in any of Claims 1 to 11, wherein the amounts of the marker reagent bound to the plural reagent immobilization parts are measured, thereby to qualitatively or quantitatively analyze the analyte in the sample solution. In the measurement method using a biosensor as defined in any of Claims 1 to 11, the measurement is carried out on the basis of the bindings of the marker reagent to the plural reagent immobilization parts.

According to the present invention, there is provided a measurement method employing a biosensor having a developing layer for developing a sample solution, and including plural reagent parts which are immobilized to portions of the developing layer, and have different affinities for an analyte in the sample solution or a marker reagent, and a reagent part which is marked and held by a portion of the developing layer, and is dissolvable by developing the sample solution; wherein the amounts of the marker reagent bound to the plural reagent immobilization parts are measured, thereby to qualitatively or quantitatively analyze the analyte in the sample solution. In the measurement method, the amounts of the marker reagent bound to the plural reagent immobilization parts are measured to qualitatively or quantitatively analyze the analyte in the sample solution, by employing a biosensor having a developing layer for developing a sample solution, and including plural reagent parts which are immobilized to portions of the developing layer, and have different affinities for an analyte in the sample solution or a marker reagent, and a reagent part which is marked and held by a portion of the developing layer, and is dissolvable by developing the sample solution. The qualitative analysis means two-step judgement represented by positive/negative judgement, and the quantitative analysis includes conversion into numerals, and semi-quantitative analysis having three or more steps.

According to Claim 13 of the present invention, in the measurement method as defined in Claim 12, the method for measuring the amounts of the marker reagent bound to the plural reagent immobilization parts employs an electromagnetic wave. In the measurement method as defined in Claim 12, an electromagnetic wave is employed in the method for measuring the amounts of the marker reagent bound to the plural reagent immobilization parts.

According to Claim 14 of the present invention, in the measurement method as defined in Claim 12 or 13, the method for measuring the amounts of the marker reagent bound to the plural reagent immobilization parts is to measure a diffused electromagnetic wave which is obtained when an electromagnetic wave is reflected. In the measurement method as defined in Claim 12 or 13, the method for measuring the amounts of the marker reagent bound to the plural reagent immobilization parts is to measure a diffused electromagnetic wave which is obtained when an applied electromagnetic wave is reflected.

According to Claim 15 of the present invention, in the measurement method as defined in any of Claims 12 to 14, an electromagnetic wave source used for the measurement is scanned with respect to the biosensor, or the biosensor is scanned with respect to the electromagnetic wave source, thereby to measure the amounts of the marker reagent bound to the reagent immobilization parts. In the measurement method as defined in any of Claims 12 to 14, when detecting the amounts of the marker reagent bound to the plural reagent immobilization parts, the electromagnetic wave source is scanned, or the biosensor is scanned.

According to the present invention, the measurement method using a biosensor is reflection absorbance measurement, wherein a light source is shaped in a line according to the plural reagent immobilization parts being shaped in lines, and the line width of the light source is 1.0 mm or shorter. In the measurement method, the method for detecting the amounts of the marker reagent bound to the plural reagent immobilization parts is to measure reflection absorbance. In this case, the electromagnetic wave is light, preferably, visible light, and the method for detecting the amounts of the marker reagent bound to the plural reagent immobilization parts is to measure diffused light which is obtained when applied visible light is reflected.

According to Claim 16 of the present invention, in the measurement method as defined in any of Claims 12 to 15, the amounts of the marker reagent bound to the plural reagent immobilization parts are respectively measured, thereby to perform prozone judgement. In the measurement method as defined in any of Claims 12 to 15, after the amounts of the marker reagent bound to the plural reagent immobilization parts are respectively measured, a prozone area is judged from one or plural results of measurements.

According to Claim 17 of the present invention, in the measurement method as defined in any of Claims 12 to 16, among the plural reagent immobilization parts, the amount of the marker reagent bound to the reagent immobilization part which is positioned on the uppermost stream side with respect to the sample solution applying part is measured; the amounts of the marker reagent bound to the other reagent immobilization parts are also measured; and, on the basis of the results of the respective measurements, the measured value of the amount of the marker reagent bound to the uppermost-stream side reagent immobilization part is subjected to prozone judgement. In the measurement method as defined in any of Claims 12 to 16, among the plural reagent immobilization parts, the amount of the marker reagent bound to the reagent immobilization part which is positioned on the uppermost stream side viewed from the sample solution applying part is measured as the analyte in the sample solution, and it is judged whether the result of measurement in the uppermost-stream side part is a prozone area or not, on the basis of the amounts of the marker reagent bound to the other reagent immobilization parts.

According to the present invention, in the measurement method, among the plural reagent immobilization parts, the amount of the marker reagent bound to the reagent immobilization part that is positioned on the uppermost stream side with respect to the sample solution applying part is measured; the amounts of the marker reagent bound to the other reagent immobilization parts are also measured; it is judged by performing arithmetic processing as to whether each of the measurement results is within a marker reagent binding amount measurement range in the uppermost-stream side reagent immobilization part or within a marker reagent binding amount measurement range in another reagent immobilization part; and one of the marker reagent binding amounts is used as a measurement result. In the measurement method, the analyte in the sample solution is measured by detecting the amounts of the marker reagent bound to the plural reagent immobilization parts are detected. Furthermore, when the analyte in the sample solution is measured on the basis of the amount of the marker reagent bound to the reagent immobilization part that is positioned on the uppermost-stream side viewed from the sample solution applying part, the amounts of the marker reagent bound to the other reagent immobilization parts are also measured, and it is judged by performing arithmetic processing as to which one of the marker reagent binding amounts obtained in the plural reagent immobilization parts, including the uppermost-stream side part, should be used for measurement of the concentration of the analyte in the sample solution, on the basis of the marker reagent binding amounts obtained in the respective reagent immobilization parts including the uppermost-stream side part, and then the analyte in the sample solution is measured on the basis of the reagent binding amount obtained in one of the reagent immobilization parts.

According to Claim 18 of the present invention, in the measurement method as defined in any of Claims 12 to 17, the measurement is one-step immunochromatography which is started by the sample solution applying operation. The measurement method defined in any of Claims 12 to 17 is carried out using a biosensor which is a one-step immunochromatography that starts measurement by the sample solution applying operation.

According to Claim 19 of the present invention, in the biosensor as defined in any of Claims 1 to 5 and 7 to 11, the reagent immobilization parts are provided in three positions. In the biosensor as defined in any of Claims 1 to 5 and 7 to 11, the reagent immobilization parts are provided in three positions.

According to Claim 20 of the present invention, in the biosensor as defined in Claim 19, the reagent immobilization part which is positioned at the uppermost stream side with respect to the sample solution applying part has the highest affinity for the analyte in the sample solution or the marker reagent, and the second and third reagent immobilization parts have the same affinity. In the biosensor as defined in Claim 19, the reagent immobilization part which is positioned at the uppermost stream side with respect to the sample solution applying part has the highest affinity for the analyte in the sample solution or the marker reagent, and the second and third reagent immobilization parts have the same affinity.

According to Claim 21 of the present invention, in the measurement method as defined in any of Claims 12 to 18, the reagent immobilization parts are provided in three positions. In the measurement method as defined in any of Claims 12 to 18, the reagent immobilization parts are provided in three positions.

According to Claim 22 of the present invention, in the measurement method employing a biosensor as defined in Claim 20, the amounts of the marker reagent bound to the plural reagent immobilization parts are measured, thereby to qualitatively or quantitatively analyze the analyte in the sample solution. In the measurement method employing a biosensor as defined in Claim 20, the amounts of the marker reagent bound to the reagent immobilization parts are measured, thereby to qualitatively or quantitatively analyze the analyte in the sample solution.

According to the present invention, in the measurement method, a prozone area is detected on the basis of the amounts of the marker reagent bound to the two reagent immobilization parts which are positioned at lower stream side with respect to the sample solution applying part, among the three reagent immobilization parts. In the measurement method, a prozone area is detected on the basis of the amounts of the marker reagent bound to the two reagent immobilization parts which are positioned at the lower stream side with respect to the sample solution applying part, among the three reagent immobilization parts.

According to Claim 1, there is provided a biosensor having a developing layer for developing a sample solution, including a reagent part immobilized to a portion of the developing layer and a marked reagent part which is held in a dry state by a portion of the developing layer, and is dissolvable by developing the sample solution, and qualitatively or quantitatively analyzing an analyte in the sample solution by measuring the amount of the marker reagent bound to the reagent immobilization part; wherein plural reagent immobilization parts exist, and the respective reagent immobilization parts have different affinities for the analyte in the sample solution or the marker reagent. Therefore, in measuring the sample solution, even when the concentration of the analyte in the solution is high, a dilution operation or the like is not needed, whereby a simple and speedy biosensor can be provided. Further, since detection of prozone area is possible, a simple, speedy, and highly precise biosensor can be obtained.

According to Claim 2, there is provided a biosensor which is a device having a developing layer for developing a sample solution, including a reagent part immobilized to a portion of the developing layer and a marked reagent part which is held in a dry state by a portion of the developing layer, and is dissolvable by developing the sample solution, and having a sample applying part on which the sample solution is applied, the marker reagent part, and the marker immobilization part which are arranged in this order, said biosensor qualitatively or quantitatively analyzing an analyte in the sample solution by measuring the amount of the marker reagent bound to the reagent immobilization part; wherein plural reagent immobilization parts exist, and the respective reagent immobilization parts have different affinities for the analyte in the sample solution or the marker reagent. Therefore, a biosensor having a wide dynamic range for the concentration of the analyte in the sample solution can be provided. Furthermore, since detection of prozone area is possible, a simple, speedy, highly precise, and highly versatile biosensor can be obtained.

According to Claim 2, in the biosensor as defined in Claim 1, the reagents immobilized to the plural reagent immobilization parts are antibodies, the analyte in the sample solution is an antigen, and an antibody having a higher affinity for the analyte in the sample solution or the marker reagent is immobilized to the reagent immobilization part that is positioned on the upper stream side with respect to the sample solution applying part. In the case of measuring the antigen, since the antibodies having different affinities for the analyte or the marker reagent are immobilized to the plural reagent immobilization parts, the antigen concentration dynamic range can be kept sufficiently wide. Further, assuming that the sample solution applying part is at the uppermost stream, the reagent immobilization part at the upper stream side has the higher affinity for the analyte or the maker reagent, whereby a biosensor with higher accuracy can be provided in the uppermost-stream reagent immobilization part, while a biosensor with higher accuracy and precision which is capable of prozone detection can be provided in the other reagent immobilization part.

According to Claim 3, in the biosensor as defined in any of Claims 1 or 2, the reagents in the plural reagent immobilization parts are monoclonal antibodies. Therefore, when biosensors are mass-produced or when plural biosensors having uniform performance are needed, plural or a large quantity of speedy and precise biosensors showing uniform performances can be produced by the uniform properties of the monoclonal antibodies, in combination with high productivity and productive stability.

According to the present invention, in the biosensor, the analyte in the sample solution is quantitatively analyzed by measuring the amount of the marker reagent bound to the plural reagent immobilization parts. The reagents on the plural reagent immobilization parts have different affinities for the analyte or the marker reagent, and the amounts of the marker reagent bound to the respective parts are not checked by fuzzy visual check but the results of measurement are converted into numerals, whereby a simple, speedy, precise, and accurate biosensor can be obtained.

According to the present invention, in the biosensor, a prozone phenomenon is detected by measuring the amount of the marker reagent bound to the plural reagent immobilization parts. Therefore, a biosensor with higher precision, which can judge whether the amount of the marker reagent bound to each reagent immobilization part is within the prozone area or not, is obtained.

According to the present invention, in the biosensor, among the plural reagent immobilization parts, the amount of the marker reagent bound to the reagent immobilization part which is positioned on the uppermost stream side with respect to the sample solution applying part is measured, thereby to measure the analyte in the sample solution; and the amounts of the marker reagent bound to the other reagent immobilization parts are also measured and, on the basis of the results of the respective measurements, the measured value of the amount of the marker reagent bound to the uppermost-steam side reagent immobilization part is subjected to prozone judgement. Therefore, assuming that the sample solution applying part is the uppermost stream, the amount of the marker reagent bound to the reagent immobilization part on the uppermost stream side among the plural reagent immobilization parts is measured, whereby highly accurate quantitative measurement is realized. Further, prozone judgement is carried out in measuring the amounts of the marker reagent bound to the other reagent immobilization parts, whereby a simple, speedy, and accurate biosensor with higher precision can be obtained.

According to Claim 4, in the biosensor as defined in any of Claims 1 to 3, the plural reagent immobilization parts have different affinities for the analyte in the sample solution or the maker reagent, whereby the respective reagent immobilization parts have different dynamic ranges for measuring the concentration of the analyte in the sample solution. Therefore, the plural reagent immobilization parts have different sample solution concentration dynamic ranges, whereby a biosensor which can measure plural analyte dynamic ranges can be obtained.

According to the present invention, in the biosensor, the plural reagent immobilization parts have different affinities for the analyte in the same solution or the marker reagent, thereby to increase the dynamic range for measuring the concentration of the analyte in the sample solution. Therefore, when measuring the amounts of the marker reagent bound to the plural reagent immobilization parts, measurement over a wider range is realized by combining the analyte concentration dynamic ranges of the respective reagent immobilization parts. Thereby, a biosensor, which can measure the analyte concentration over a wide range by onetime measurement without requiring a complicated operation such as dilution, can be obtained.

According to Claim 5, in the biosensor as defined in any of Claims 1 to 4 the plural reagent immobilization parts recognize the same epitope. Therefore, even when the reaction mode in each of the plural reagent immobilization parts is any of "marker reagent-immobilized reagent", "marker reagent", and "analyte-immobilized reagent", a stable, simple, precise, and speedy biosensor, in which stereoscopic damage relating to the reaction in molecular level is small, can be obtained.

According to Claim 6, in the biosensor as defined in any of Claims 1 to 5, the reagent immobilization parts are provided in two positions. Therefore, the dynamic range for analyte concentration is increased, and a minimum reagent composition that enables prozone detection is realized, whereby a cheaper, speedy, simple, and precise biosensor can be obtained.

According to Claim 7, in the biosensor as defined in any of Claims 1 to 6, the plural reagent immobilization parts are in contact with each other. Although the development of the sample solution on the reagent immobilization parts generally becomes non-uniform, the plural reagent immobilization parts are apparently united into one, resulting in a highly accurate biosensor having a wide analyte dynamic range and being able to perform prozone detection, in which penetration of the sample solution that develops the developing layer is kept more uniform.

According to Claim 9, in the biosensor as defined in any of Claims 1 to 7, the developing layer employs a lateral flow system, the plural reagent immobilization parts are immobilized in lines along a direction perpendicular to the sample solution developing direction, the line width is 0.5 mm~2.0 mm, and the intervals between the lines of the plural reagent immobilization parts are 1.0 mm or longer. When the sample solution develops the plural reagent immobilization parts on the developing layer, the development is apt to be non-uniform. However, since the line width is 0.5 mm~2.0 mm, the development can be visually checked while suppressing the adverse effect of non-uniform development. Further, since the intervals between the reagent immobilization parts are 1.0 mm or more, the respective parts can be visually distinguished from each other. Therefore, a simpler, speedier, highly accurate and precise biosensor having excellent viewability can be obtained. This is applicable to the above-mentioned biosensor employing an optical measurement device.

According to Claim 9, in the biosensor as defined in any of Claims 1 to 8, all of the reagents including the marker reagent and the immobilized reagents are in their dry states. Since the plural reagent immobilization parts have different affinities for the analyte or the marker reagent, a biosensor having a sufficiently wide dynamic range for the analyte concentration, and a function of detecting a prozone area can be obtained. Moreover, since all of the reagents are in their perfect dry states, a biosensor which has excellent shelf life and stability and is easily portable can be obtained.

According to Claim 10, in the biosensor as defined in any of Claims 1 to 9, the sample solution is urine, saliva, or blood. Therefore a highly precise, simple, and speedy biosensor can be provided in the field of clinical examination where speedy reaction is desired.

According to Claim 11, the biosensor as defined in any of Claims 1 to 10 is used immunochromatography. Therefore, in the immunochromatography which is becoming widespread on the market as a simple immunomeasurement method, a highly-precise biosensor which prevents the user from performing false judgement, and realizes an operation as simple as that of the conventional immunochromatography, can be obtained.

According to Claim 12, in the measurement method employing a biosensor as defined in any of Claims 1 to 11, the amounts of the marker reagent bound to the plural reagent immobilization parts are measured, thereby to qualitatively or quantitatively analyze the analyte in the sample solution. Therefore, even when the concentration of the analyte in the sample solution is high, a dilution operation or the like is not needed in measuring the sample solution, whereby a simple and speedy measurement method can be obtained. Furthermore, since detection of prozone areas is possible, a simple, speedy, yet highly precise measurement can be realized.

According to the present invention, there is provided a measurement method employing a biosensor having a developing layer for developing a sample solution, and including plural reagent parts which are immobilized to portions of the developing layer, and have different affinities for an analyte in the sample solution or a marker reagent, and a reagent part which is marked and held by a portion of the developing layer, and is dissolvable by developing the sample solution; wherein the amounts of the marker reagent bound to the plural reagent immobilization parts are measured, thereby to qualitatively or quantitatively analyze the analyte in the sample solution. Therefore, even when the concentration of the analyte in the sample solution is high, a dilution operation or the like is not needed in measuring the sample solution, whereby simple and speedy measurement can be realized. Furthermore, since detection of prozone areas is possible, simple, speedy, yet highly precise measurement can be realized.

According to Claim 13, in the measurement method as defined in Claim 12, the method for measuring the amounts of the marker reagent bound to the plural reagent immobilization parts employs an electromagnetic wave. Therefore, it is possible to realize a measurement method in which the dynamic range for analyte concentration is wide, prozone detection is possible, and more precise judgement not by visual observation but by numerical expression can be carried out.

According to Claim 14, in the measurement method as defined in Claim 12 or 13, the method for measuring the amounts of the marker reagent bound to the plural reagent immobilization parts is to measure a diffused electromagnetic wave obtained when an electromagnetic wave is reflected. Therefore, it is possible to realize a measurement method in which the dynamic range for analyte concentration is wide, prozone detection is possible, and more precise judgement not by visual observation but by numerical expression can be carried out, by using a more miniaturizable technique with a light source and a photodetector being provided in the same direction.

According to Claim 15, in the measurement method as defined in any of Claims 12 to 14, an electromagnetic wave source used for the measurement is scanned with respect to the biosensor, or the biosensor is scanned with respect to the electromagnetic wave source, thereby to measure the amounts of the marker reagent bound to the reagent immobilization parts. Therefore, it is possible to provide a more precise and accurate measurement method in which the marker reagent on the plural reagent immobilization parts is detected as signals for the developing layer other than the plural reagent immobilization parts to eliminate influences of factors which are not caused by the analyte concentration, and further, the amounts of the marker reagent bound to the plural reagent immobilization parts can be detected precisely.

According to the present invention, the measurement method employing a biosensor is reflection absorbance measurement, wherein a light source is shaped in a line according to the plural reagent immobilization parts being shaped in lines, and the line width of the light source is 1.0 mm or shorter. Therefore, it is possible to realize a precise and accurate measurement method in which the dynamic range for analyte concentration is wide, prozone detection is possible, energy consumption is reduced by the light source of 1.0 mm or shorter, and influence of noise to the amounts of the marker reagent bound to the plural reagent immobilization parts is reduced. Preferably, in the above-described biosensor, the width of the light source is equal to the width of each reagent immobilization part, and shorter than the spacing between the plural reagent immobilization parts.

According to Claim 16, in the measurement method as defined in any of Claims 12 to 15, the amounts of the marker reagent bound to the plural reagent immobilization parts are respectively measured, thereby to perform prozone judgement. Therefore, in measuring the amounts of the marker reagent bound to the plural reagent immobilization parts, since the amount of the marker reagent bound to each reagent immobilization part is measured, judgement as to whether the measurement is within a prozone area or not can be carried out.

According to Claim 17, in the measurement method as defined in any of Claims 12 to 16, among the plural reagent immobilization parts, the amount of the marker reagent bound to the reagent immobilization part which is positioned on the uppermost stream side with respect to the sample solution applying part is measured; the amounts of the marker reagent bound to the other reagent immobilization parts are also measured; and, on the basis of the results of the respective measurements, the measured value of the amount of the marker reagent bound to the uppermost-stream side reagent immobilization part is subjected to prozone judgement. Therefore, assuming that the sample solution applying part is the uppermost stream, the amount of the marker reagent bound to the reagent immobilization part positioned at the uppermost stream side among the plural reagent immobilization parts is measured, whereby highly accurate quantitative measurement is realized. Further, prozone judgement is carried out in measuring the amounts of the marker reagent bound to the other reagent immobilization parts, whereby simple, speedy, and accurate measurement with higher precision can be realized.

According to the present invention, in the measurement method, among the plural reagent immobilization parts, the amount of the marker reagent bound to the reagent immobilization part that is positioned on the uppermost stream side with respect to the sample solution applying part is measured; the amounts of the marker reagent bound to the other reagent immobilization parts are also measured; it is judged by performing arithmetic processing as to whether each of the measurement results is within a marker reagent binding amount measurement range in the uppermost-stream side reagent immobilization part or within a marker reagent binding amount measurement range in another reagent immobilization part; and one of the marker reagent binding amounts is used as a measurement result. Therefore, the respective reagent immobilization parts have different sample solution concentration dynamic ranges, whereby plural analyte dynamic ranges can be measured.

According to Claim 18, in the measurement method as defined in any of Claims 12 to 17, the measurement is one-step immunochromatography which is started by the sample solution applying operation. Therefore, the advantage of the simple and speedy one-step immunochromatography, which requires no cleaning operation although it is an immunomeasurement method, is maintained, and prozone detection is possible, whereby a measurement method with higher precision can be provided. Further, a measurement method which can measure a wider range of analyte concentration using only similar measurement operation can be provided.

According to Claim 19, in the biosensor as defined in any of Claims 1 to 5 and 7 to 11, the reagent immobilization parts are provided in three positions. Therefore, a reagent composition which has a precise and reliable dynamic range for analyte concentration and enables prozone detection is realized, whereby a speedier and simpler biosensor having higher precision and reliability can be obtained.

According to Claim 20, in the biosensor as defined in Claim 19, the reagent immobilization part which is positioned at the uppermost stream side with respect to the sample solution applying part has the highest affinity for the analyte in the sample solution or the marker reagent, and the second and third reagent immobilization parts have the same affinity. Therefore, a reagent composition which has a precise and reliable dynamic range for analyte concentration and enables prozone detection is realized. Further, the reagent immobilization parts are provided in three positions while they are composed of two kinds of reagents, whereby a biosensor which is cheaper due to the less reagent composition and is highly precise and reliable due to the three reagent immobilization parts, can be obtained.

According to Claim 21, in the measurement method as defined in any of Claims 12 to 18, signals from the three reagent immobilization parts can be obtained. Therefore, a precise, reliable, speedy, and simple measurement method can be realized.

According to Claim 22, in the measurement method employing a biosensor as defined in Claim 20, the reagent immobilization parts are provided in three positions while they are composed of two kinds of reagents. Therefore, a measurement method which is cheaper due to the less reagent composition and is highly precise and reliable due to the three reagent immobilization parts, can be realized.

According to the present invention, in the measurement method, a prozone area is detected on the basis of the amounts of the marker reagent bound to the two reagent immobilization parts which are positioned at lower stream side with respect to the sample solution applying part, among the three reagent immobilization parts. Therefore, a precise, reliable, speedy, and simple measurement method can be realized.

BRIEF DESCRIPTION OF THE DRAWINGS

FIG. 5(*a*) is a schematic diagram illustrating a measurement dynamic range according to the first embodiment of the invention, and FIG. 5(*b*) is a schematic diagram illustrating prozone judgement according to the first embodiment of the invention.

BEST MODE TO EXECUTE THE INVENTION

Embodiment 1

Figure 1:
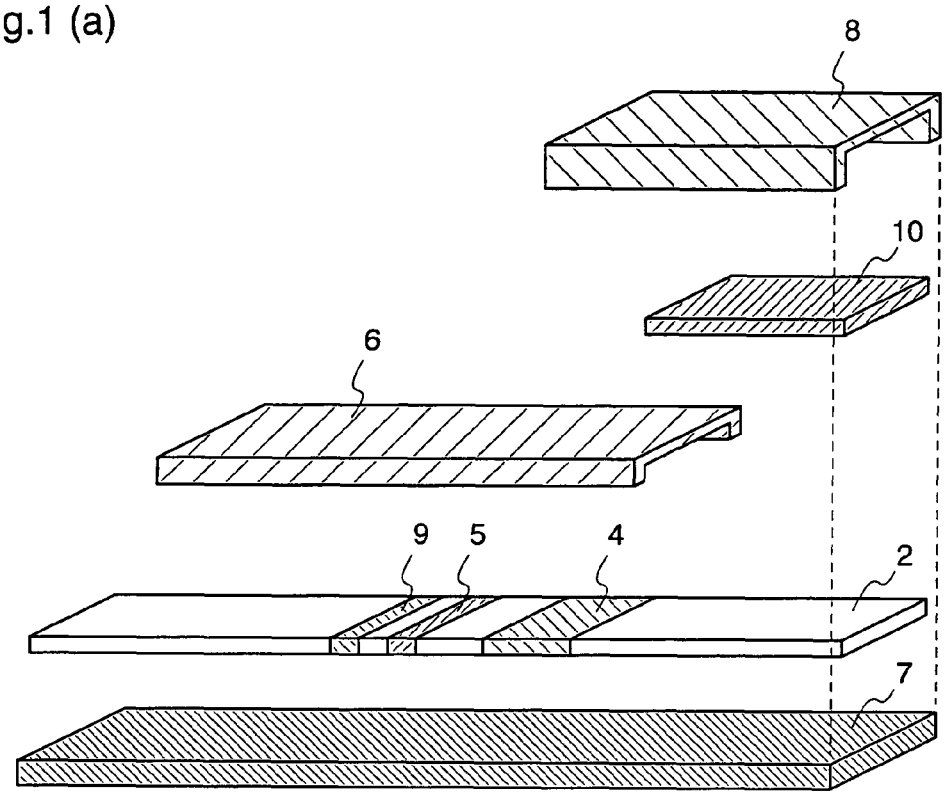
FIG. 1(*a*) is an exploded view illustrating a biosensor according to a first embodiment of the invention, and FIG. 1(*b*) is a perspective view illustrating the biosensor according to the first embodiment.
Figure 1:
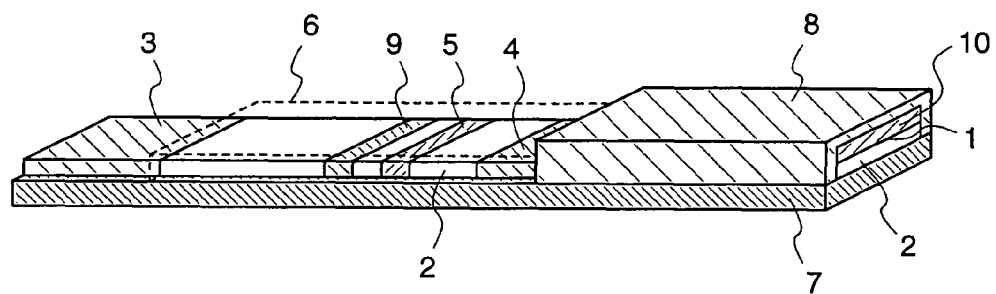

Hereinafter, a first embodiment of the present invention will be described with reference to FIG. 1. FIG. 1(a) is an exploded view of a biosensor according to the first embodiment of the present invention, and FIG. 1(b) is a perspective view of the biosensor according to the first embodiment. In FIG. 1, reference numeral 2 denotes a developing layer comprising nitrocellulose. The developing layer may comprise an arbitrary porous material that can be wetted by a sample solution, such as a filter paper, nonwoven fabric, membrane, fabric, or fiberglass. Reference numeral 4 denotes a marker reagent in which a gold colloid marker antibody against an analyte in the sample solution is held in a dry state so as to be dissolvable by the sample solution. Reference numerals 5 and 9 denote a reagent immobilization part I and a reagent immobilization part II, respectively, which are antibodies against the analyte in the sample solution. Both of these antibodies are bound to the analyte with epitopes different from that of the marker reagent, and they are immobilized in their dry states so as to form complexes with the analyte in the sample solution and the marker reagent. Further, the antibody used for the reagent immobilization part I and the antibody used for the reagent immobilization part II have different affinities for the analyte in the sample solution. Since a reagent immobilization part, which is positioned at the upper-stream side viewed from a part onto which the sample solution is applied, comes in contact with the sample solution and the analyte earlier than the other reagent immobilization part, it is desired to be made of an antibody having higher affinity for the analyte. Any antibodies may be used for the reagent immobilization parts I and II so long as ternary complexes comprising the antibody, the marker reagent, and the analyte can be formed, and therefore, the epitopes of the antibodies for the analyte may be the same or different from each other. Furthermore, while in FIG. 1 two reagent immobilization parts are provided, the number of the reagent immobilization parts is not necessarily two. The number of the reagent immobilization parts may be arbitrarily selected according to the purpose so long as it is two or more. Further, the shapes of the reagent immobilization parts on the developing layer are not necessarily lines. Any shape, such as spots, characters, or keys, may be arbitrarily selected. Furthermore, while in FIG. 1 the reagent immobilization parts 5 and 9 are spatially apart from each other, these parts are not necessarily apart from each other, but may be in contact with each other so that they appear to be a single line. Moreover, the marking method described here is selected as means for detecting bindings in the reagent immobilization parts, and gold colloid is merely an example. Any marker may be arbitrarily selected according to the needs of the user, for example, enzymes, proteins, dyes, fluorochromes, and colored particles such as latex may be employed. Reference numeral 6 denotes a liquid impermeable sheet comprising a transparent PET tape. The liquid impermeable sheet 6 hermetically covers the developing layer 2 except a portion contacting a fine space 1 and an end portion to which the sample solution reaches. Since the developing layer 2 is covered with the liquid impermeable sheet 6, dropping of the sample solution onto part other than the solution applying part is avoided, and contamination from the outside is also avoided. The contamination from the outside indicates accidental contact of the sample solution, direct touch of patient's hand to the developing layer, and the like. Preferably, the developing layer is covered with a transparent material. It is desired that at least a portion covering the reagent immobilization part 5 is transparent because the result of measurement is checked through this portion. Further, when measurement with higher accuracy is required, an upper portion of the developing layer including the marker reagent part and the reagent immobilization parts may be hermetically sealed and, further, side surfaces parallel to the direction in which the sample solution penetrates may be hermetically sealed as well. Reference numeral 3 denotes an opening part of the developing layer, and numeral 7 denotes a substrate for holding the developing layer, which comprises a white PET film. The substrate 7 has the function of reinforcing the developing layer as well as the function of blocking the sample solution when a sample having the risk of infection, such as blood, saliva, or urine, is used as the sample solution. Further, when there is a possibility that the developing layer becomes transparent to light when it is wetted, the substrate 7 may have the effect of shutting light. Reference numeral 8 denotes a fine space formation member, which has the function of forming a space into which the sample solution flows due to capillary phenomenon, and comprises laminated transparent PET films. The fine space formation member 8 also has the function of preventing the sample solution from contaminating the outside when handling the biosensor after application of the sample solution. The contamination indicates accidental adhesion or scattering of the sample solution. The fine space formation member 8 may be made of a synthetic resin material such as ABS, polystyrene, or polyvinyl chloride, or a solution impermeable material such as metal or glass. Although the fine space formation member 8 is preferably transparent or semi-transparent, it may be made of an arbitrary colored or opaque material. Reference numeral 1 denotes a fine space formed by the fine space formation member 8, into which the sample solution flows due to capillary phenomenon. The fine space 1 is connected to the developing layer 2, and penetration of the sample solution into the developing layer 2 is started when the solution flows into the fine space 1.

Next, measurement of the sample solution will be described with reference to FIG. 1(b). When the sample solution is brought into contact with the fine space 1, the sample solution naturally flows into the fine space by capillary phenomenon without the necessity of mechanical operation. Whether the amount of flow of the sample solution is sufficient or not can be checked through the fine space formation member. In the case where the amount of sample solution to be applied is restricted, when a predetermined volume of sample solution is required, the volume of the fine space is set to the predetermined volume, thereby to accurately restrict the amount of sample solution to be applied. Further, when a predetermined volume of or more sample solution is required, the volume of the fine space is set according to the required volume, whereby the amount of sample solution to be applied can be controlled as desired. A cell contraction agent 10 is held in the fine space, and potassium chloride is employed in this example. The cell contraction agent 10 is a reagent to be provided when cell components are included in the sample solution. It is not especially needed when using a sample solution including no cell components. Further, the cell contraction agent (cell component contraction agent) 10 may be any reagent so long as it has the effect of contracting cells, for example, inorganic compound including inorganic salt other than potassium chloride, sodium chloride, sodium phosphate salt, and the like, amino acid such as glycine or glutamic acid, imino acid such as proline, saccharide such as glucose, sucrose, or trehalose, or sugar alcohol such as glucitole. A system including such cell contraction agent (cell component contraction agent) 10 is especially effective when whole blood is used as a sample solution. The sample solution drawn into the fine space penetrates in the developing layer from the portion where the fine space is in contact with the developing layer. When the sample solution reaches the marker reagent 4, dissolution of the marker reagent 4 is started. When the analyte exists in the sample solution, penetration is promoted while the gold colloid marker antibody reacts with the analyte, and the sample solution reaches the reagent immobilization part I(5). When the analyte exists in the sample solution, complexes of the immobilized antibody I, the analyte, and the marker antibody are formed in accordance with the amount of the analyte. Next, the sample solution reaches the reagent immobilization part II(9). When the analyte exists in the sample solution, complexes of the immobilized antibody II, the analyte, and the marker antibody are formed in accordance with the amount of the analyte, with respect to the marker reagent 4 which has not been bound onto the reagent immobilization part 5. As for binding of the marker antibody onto the reagent immobilization parts, the greater part of the marker antibody passes through the reagent immobilization parts without being bound thereto when no analyte exists or when the amount of the analyte is lower than the detection sensitivity. The marker antibody reaches the opening part 3 of the developing layer. Since the opening part 3 is not covered with the opaque sheet but is open, the sample solution is volatilized or evaporated after it has reached the opening part 3 or while reaching the opening part 3. Further, the sample solution exudes onto the opening part, and the sample solution on the developing layer in the opening part reaches up to the same or corresponding height as/to the sample solution on the developing layer in the fine space. Due to these effects, penetration of the sample solution in the developing layer is controlled in a predetermined direction during measurement without requiring a material for absorption. Generally, an absorption part is often provided instead of the opening part. The reason is as follows. When a porous material having higher water-holding effect and absorption effect is used as a material for the reaction part of the developing layer, the sample solution is efficiently absorbed and sucked, and further, the sample solution on the developing layer can be passed through and the measurement time can be reduced. The opening part 3 has the effects similar to those mentioned above, and the technique of using the fine space or the opening part is particularly suitable for the case where the sample solution is very small in quantity. That is, it is particularly suitable for the case where the sample solution is very small in quantity, such as blood obtained by piercing a finger or the like. Next, the result of measurement is obtained by checking the binding state of the marker reagent on the reagent immobilization part I(5), and the reagent immobilization part II(9). When qualitative determination is required, visual observation is also possible. When measurement with higher precision is required, the side surfaces of the developing layer parallel to the sample solution penetrating direction and the upper surface of the developing layer are hermetically sealed with a liquid impermeable material to rectify the penetration of the sample solution, whereby a uniform amount of complexes are formed according to the amount of the analyte in the sample solution, and a quantitative result can be obtained by measuring the amount of binding of the marker by using, for example, reflected light or transmitted light of a diffused electromagnetic wave including reflection absorbance. The electromagnetic wave is preferably a visible region or a near-visible region, and it is selectable according to the needs of the user, for example, LED (Light Emitting Diode) or LD (Laser Diode) can be selected. Further, the reagent immobilization part I may be used for detection of the concentration of the analyte in the sample solution, and the amount of the marker reagent bound to the reagent immobilization part II(9) may be used for prozone detection by using an antibody of lower affinity. Furthermore, while the sandwich reaction in the antigen-antibody reaction has been described, a competitive reaction is also possible when a reagent that competitively reacts with the analyte in the sample solution is selected. Further, when a specific binding reaction other than the antigen-antibody reaction is desired, the biosensor can be constituted by reagent components of systems forming arbitrary binding reactions.

Embodiment 2

Figure 6:
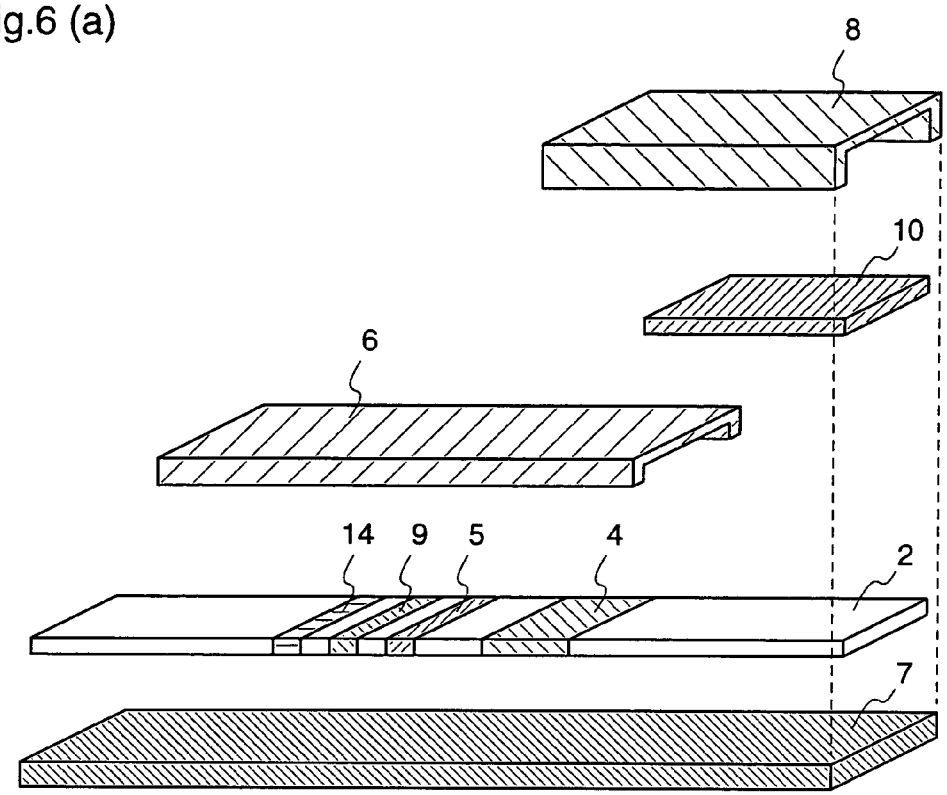
FIG. 6(*a*) is an exploded view illustrating a biosensor according to a second embodiment of the invention wherein three reagent immobilization parts are provided, and FIG. 6(*b*) is a perspective view illustrating the biosensor according to the second embodiment.
Figure 6:
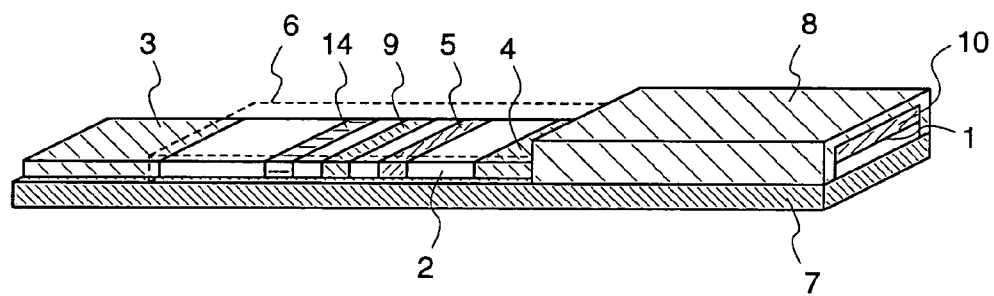

Hereinafter, a second embodiment of the present invention will be described with reference to FIG. 6. FIG. 6(*a*) is an exploded view of a biosensor according to the second embodiment of the present invention, and FIG. 6(*b*) is a perspective view of the biosensor according to the second embodiment. In FIG. 6, reference numeral 2 denotes a developing layer comprising nitrocellulose. The developing layer may comprise an arbitrary porous material that can be wetted by a sample solution, such as a filter paper, nonwoven fabric, membrane, fabric, or fiberglass. Reference numeral 4 denotes a marker reagent in which a gold colloid marker antibody against an analyte in the sample solution is held in a dry state so as to be dissolvable by the sample solution. Reference numerals 5, 9, 14 denote a reagent immobilization part I, a reagent immobilization part II, and a reagent immobilization part III, respectively, which are antibodies against the analyte in the sample solution. These antibodies are immobilized in their dry states so as to form complexes with the analyte in the sample solution and the marker reagent. Further, the antibody used for the reagent immobilization part I and the antibody used for the reagent immobilization parts II and III have different affinities for the analyte in the sample solution. Since a reagent immobilization part, which is positioned at the upper-stream side viewed from a part onto which the sample solution is applied, comes in contact with the sample solution and the analyte earlier than the other reagent immobilization part, it is desired to be made of an antibody having higher affinity for the analyte. Any antibodies may be used for the reagent immobilization parts I, II, and III so long as ternary complexes comprising the antibody, the marker reagent, and the analyte can be formed, and therefore, the epitopes of the antibodies for the analyte may be the same or different from each other. Furthermore, while FIG. 6 shows the case where three reagent immobilization parts are provided, this is particularly effective when the measurement dynamic range in the first embodiment where two reagent immobilization parts are provided is enlarged, and prozone detection after enlargement is realized, and furthermore, the measurement dynamic range can be further enlarged. As already described for the case of providing two reagent immobilization parts, when a wider measurement dynamic range is desired or when a relatively narrow measurement dynamic range is required in each reagent immobilization part and further the measurement dynamic range should be maintained by varying the affinity of the reagent immobilization part, the number of the reagent immobilization parts is not necessarily three. The number of the reagent immobilization parts may be arbitrarily selected according to the purpose so long as it is three or more. Further, when three or more reagent immobilization parts are used, all of the three or more reagent immobilization parts may have different affinities, or two kinds of reagents having different affinities may be combined. In this case, it is needless to say that the combination of the reagent immobilization parts may be arbitrarily selected according to the purpose of the user. The shapes of the reagent immobilization parts on the developing layer are not necessarily lines. Any shape, such as spots, characters, or keys, may be arbitrarily selected. Furthermore, although in FIG. 6 the reagent immobilization parts are spatially apart from each other, these parts are not necessarily apart from each other, but may be in contact with each other so that they appear to be a single line. Moreover, the marking method described here is selected as means for detecting bindings in the reagent immobilization parts, and gold colloid is merely an example. Any marker may be arbitrarily selected according to the needs of the user, for example, enzymes, proteins, dyes, fluorochromes, and colored particles such as latex may be employed. Reference numeral 6 denotes a liquid impermeable sheet comprising a transparent PET tape. The liquid impermeable sheet 6 hermetically covers the developing layer 2 except a portion contacting a fine space 1 and an end portion to which the sample solution reaches. Since the developing layer 2 is covered with the liquid impermeable sheet 6, dropping of the sample solution onto part other than the solution applying part is avoided, and contamination from the outside is also avoided. The contamination from the outside indicates accidental contact of the sample solution, direct touch of patient's hand to the developing layer, and the like. Preferably, the developing layer is covered with a transparent material, and it is desired that at least portions covering the reagent immobilization part I(5), the reagent immobilization part II(9), and the reagent immobilization part III(14) are transparent because the result of measurement is checked through these portions. Further, when measurement with higher accuracy is required, an upper portion of the developing layer including the marker reagent part and the reagent immobilization parts may be hermetically sealed and, further, side surfaces parallel to the direction in which the sample solution penetrates may be hermetically sealed as well. Reference numeral 3 denotes an opening part of the developing layer, and numeral 7 denotes a substrate for holding the developing layer, which comprises a white PET film. The substrate 7 has the function of reinforcing the developing layer as well as the function of blocking the sample solution when a sample having the risk of infection, such as blood, saliva, or urine, is used as the sample solution. Further, when there is a possibility that the developing layer becomes transparent to light when it is wetted, the substrate 7 may have the effect of shutting light. Reference numeral 8 denotes a fine space formation member, which has the function of forming a space into which the sample solution flows due to capillary phenomenon, and comprises laminated transparent PET films. The fine space formation member 8 also has the function of preventing the sample solution from contaminating the outside when handling the biosensor after application of the sample solution. The contamination indicates accidental adhesion or scattering of the sample solution. The fine space formation member 8 may be made of a synthetic resin material such as ABS, polystyrene, or polyvinyl chloride, or a solution impermeable material such as metal or glass. Although the fine space formation member 8 is preferably transparent or semi-transparent, it may be made of an arbitrary colored or opaque material. Reference numeral 1 denotes a fine space formed by the fine space formation member 8, into which the sample solution flows due to capillary phenomenon. The fine space 1 is connected to the developing layer 2, and penetration of the sample solution into the developing layer 2 is started when the solution flows into the fine space 1.

Next, measurement of the sample solution will be described with reference to FIG. 6(*b*). When the sample solution is brought into contact with the fine space 1, the sample solution naturally flows into the fine space by capillary phenomenon without the necessity of mechanical operation. Whether the amount of flow of the sample solution is sufficient or not can be checked through the fine space formation member. In the case where the amount of sample solution to be applied is restricted, when a predetermined volume of sample solution is required, the volume of the fine space is set to the predetermined volume, thereby to accurately restrict the amount of sample solution to be applied. Further, when a predetermined volume of or more sample solution is required, the volume of the fine space is set according to the required volume, whereby the amount of sample solution to be applied can be controlled as desired. A cell contraction agent 10 is held in the fine space, and potassium chloride is employed in this example. The cell contraction agent 10 is a reagent to be provided when cell components are included in the sample solution. It is not especially needed when using a sample solution including no cell components. Further, the cell contraction agent (cell component contraction agent) 10 may be any reagent so long as it has the effect of contracting cells, for example, inorganic compound including inorganic salt other than potassium chloride, sodium chloride, sodium phosphate salt, and the like, amino acid such as glycine or glutamic acid, imino acid such as proline, saccharide such as glucose, sucrose, or trehalose, or sugar alcohol such as glucitole. A system including such cell contraction agent (cell component contraction agent) 10 is especially effective when whole blood is used as a sample solution. The sample solution drawn into the fine space penetrates in the developing layer from the portion where the fine space is in contact with the developing layer. When the sample solution reaches the marker reagent 4, dissolution of the marker reagent 4 is started. When the analyte exists in the sample solution, penetration is promoted while the gold colloid marker antibody reacts with the analyte, and the sample solution reaches the reagent immobilization part I(5). When the analyte exists in the sample solution, complexes of the immobilized antibody I, the analyte, and the marker antibody are formed in accordance with the amount of the analyte. Next, the sample solution reaches the reagent immobilization part II(9). When the analyte exists in the sample solution, complexes of the immobilized antibody II, the analyte, and the marker antibody are formed in accordance with the amount of the analyte, with respect to the marker reagent 4 which has not been bound onto the reagent immobilization part 5. Further, the sample solution reaches the reagent immobilization part III(14). When the analyte exists in the sample solution, complexes of the immobilized antibody III, the analyte, and the marker antibody are formed in accordance with the amount of the analyte, with respect to the marker reagent 4 which has not been bound onto the reagent immobilization part I(5) and the reagent immobilization part II(9). As for binding of the marker antibody onto the reagent immobilization parts, the greater part of the marker antibody passes through the reagent immobilization parts without being bound thereto when no analyte exists or when the amount of the analyte is lower than the detection sensitivity. The marker antibody reaches the opening part 3 of the developing layer. Since the opening part 3 is not covered with the opaque sheet but is open, the sample solution is volatilized or evaporated after it has reached the opening part 3 or while reaching the opening part 3. Further, the sample solution exudes onto the opening part, and the sample solution on the developing layer in the opening part reaches up to the same or corresponding height as/to the sample solution on the developing layer in the fine space. Due to these effects, penetration of the sample solution in the developing layer is controlled in a predetermined direction during measurement without requiring a material for absorption. Generally, an absorption part is often provided instead of the opening part. The reason is as follows. When a porous material having higher water-holding effect and absorption effect is used as a material for the reaction part of the developing layer, the sample solution is efficiently absorbed and sucked, and further, the sample solution on the developing layer can be passed through and the measurement time can be reduced. The opening part 3 has the effects similar to those mentioned above, and the technique of using the fine space or the opening part is particularly suitable for the case where the sample solution is very small in quantity. That is, it is particularly suitable for the case where the sample solution is very small in quantity, such as blood obtained by piercing a finger or the like. Next, the result of measurement is obtained by checking the binding state of the marker reagent on the reagent immobilization part I(5), and the reagent immobilization part II(9) and the reagent immobilization part III(14). When qualitative determination is required, visual observation is also possible. When measurement with higher precision is required, the side surfaces of the developing layer parallel to the sample solution penetrating direction and the upper surface of the developing layer are hermetically sealed with a liquid impermeable material to rectify the penetration of the sample solution, whereby a uniform amount of complexes are formed according to the amount of the analyte in the sample solution, and a quantitative result can be obtained by measuring the amount of binding of the marker by using, for example, reflected light or transmitted light of a diffused electromagnetic wave including reflection absorbance. The electromagnetic wave is preferably a visible region or a near-visible region, and it is selectable according to the needs of the user, for example, LED (Light Emitting Diode) or LD (Laser Diode) can be selected. Further, the reagent immobilization part I(5) may be used for detection of the concentration of the analyte in the sample solution, and the amounts of the marker reagent bound to the reagent immobilization part II(9) and the reagent immobilization part III(14) may be used for prozone detection by using an antibody of lower affinity. Furthermore, while the sandwich reaction in the antigen-antibody reaction has been described, a competitive reaction is also possible when a reagent that competitively reacts with the analyte in the sample solution is selected. Further, when a specific binding reaction other than the antigen-antibody reaction is desired, the biosensor can be constituted by reagent components of systems forming arbitrary binding reactions.

Example

Hereinafter, a method for executing the present invention will be described in more detail using an example that follows. However, the present invention is not restricted to the following example.

(Quantitative Analysis 1 of Whole Blood CRP)

An immunochromatography test specimen including a reagent immobilization part I obtained by immobilizing an anti-CRP antibody A on a nitrocellulose film, a reagent immobilization part II obtained by immobilizing an anti-CRP antibody B on the nitrocellulose film, and a marker reagent which holds complexes of anti-CRP antibody C and gold colloid, is manufactured. This immunochromatography test specimen is shown in FIG. 1. In FIG. 1, the immunochromatography test specimen includes reagent immobilization parts I(5) and II(9) on which antibodies are immobilized, a marker reagent 4 as an area containing complexes of anti-CRP antibody C and gold colloid, which is closer to a developing start point onto which a sample solution is dropped than the reagent immobilization parts, and a sample solution introduction part 1. This immunochromatography test specimen is manufactured as follows.

a) Preparation for Immunochromatography Test Specimen

An anti-CRP antibody A solution which was diluted with a phosphate buffer solution to control the concentration was prepared. This antibody solution was applied on a nitrocellulose film by using a solution discharge device. Thereby, an antibody immobilization line I as a reagent immobilization part is obtained on the nitrocellulose film. Next, an anti-CRP antibody B having an affinity lower than that of the antibody used for the antibody immobilization line I was applied on a part 2 mm apart downstream from the sample solution introduction part. After being dried, the nitrocellulose film was immersed in a Tris-HCl buffer solution containing 1% skim milk, and shaken gently for 30 minutes. 30 minutes later, the film was moved into a Tris-HCl buffer solution tank and shaken gently for 10 minutes, and thereafter, the film was shaken gently for another 10 minutes in another Tris-HCl buffer solution tank, thereby to wash the film. After being washed twice, the film was taken out of the solution tank, and dried at room temperature.

The gold colloid was prepared by adding a 1% citric acid solution to a 0.01 gold chloride acid solution that is refluxing at 100° C. After the reflux was continued for 30 minutes, the solution was cooled at room temperature. Then, the anti-CRP antibody C was added to the gold colloid solution that was adjusted to pH 9 by a 0.2M potassium carbonate solution, and the solution was shaken for several minutes. Thereafter, a 10% BSA (bovine serum albumin) solution of pH 9 was added to the solution by such an amount that the concentration finally became 1%, and the solution was stirred, thereby to prepare an antibody-gold colloid complex (marker antibody) as a material to be detected. The marker antibody solution was subjected to centrifugation at 4° C. and 20000 G for 50 minutes to isolate the marker antibody. Then, the isolated marker antibody was suspended in a wash and buffer solution (1% BSA·phosphate buffer solution) and then subjected to centrifugation under the above-mentioned condition, thereby to wash and isolate the marker antibody. The marker antibody was suspended in a wash and buffer solution, and filtered through a 0.8 μm filter. Thereafter, the obtained marker antibody solution was prepared to an amount one-tenth as much as the original gold colloid solution, and stored at 4° C. The gold colloid marker antibody solution was set in a solution discharge device, and applied to portions apart from the immobilization line I and the immobilization line II on the anti-CRP antibody A and anti-CRP antibody B immobilized dry film, so as to have a positional relationship of the marker antibody, the immobilization line I, and the immobilization line II in this order from the sample solution application start position, and thereafter, the film was dried by vacuum freeze-dry. Thereby, a reaction layer carrier having the marker reagent on the immobilization film is obtained.

Next, the reaction layer carrier having the prepared marker reagent is affixed to a substrate comprising 0.5 mm thick white PET, and the substrate was cut into 5.0 mm parts (specimens). After the cutting, a 100 μm thick transparent tape is wound around each specimen from the marker antibody holding part to the end part. Then, a space formation member formed by laminating 100 μm thick transparent PET was affixed onto a center portion of the beginning part around which no transparent tape is wound, thereby forming a space part (5.0 mm wide×12.0 mm long×0.5 mm high). A potassium chloride solution prepared to 1.5M was dropped onto the space formation member, and thereafter, the space formation member was immediately frozen by liquid nitrogen to be freeze-dried, thereby forming the space formation member having the contraction agent holding part where potassium chloride is held in the dry state. Thus, the immunochromatography test specimen was manufactured.

b) Preparation of Sample

Human blood to which EDTA·2K was added as an anticoagulant was prepared so as to have a hematocrit value of 45%. CRP solutions of known concentrations were added to this blood to prepare CRP containing bloods having various known concentrations.

c) Measurement of Degree of Coloration on Test Specimen

Figure 2:
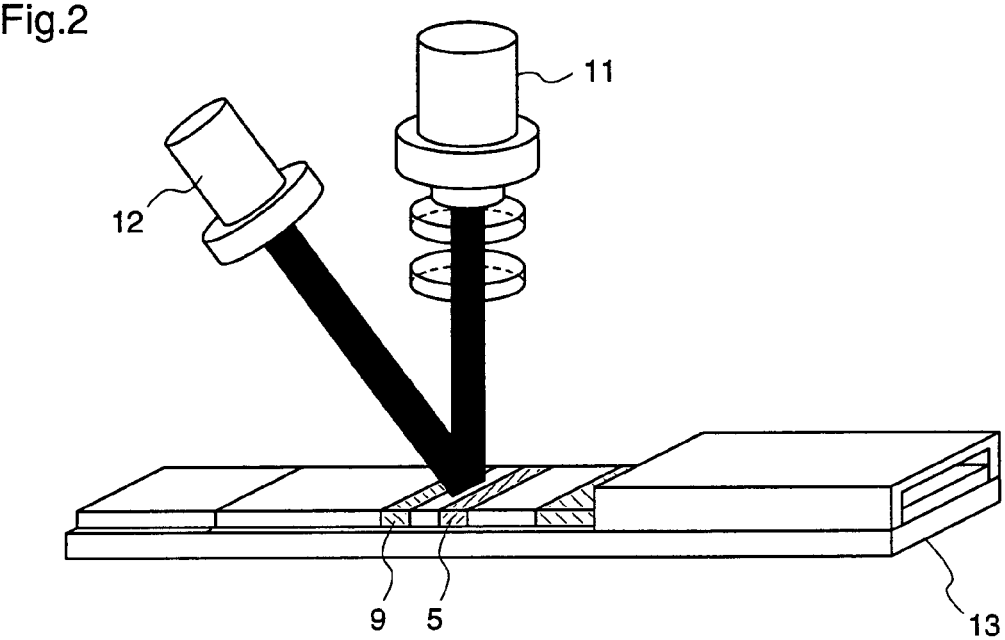
FIG. 2 is a diagram illustrating measurement according to the first embodiment of the invention.
Figure 3:
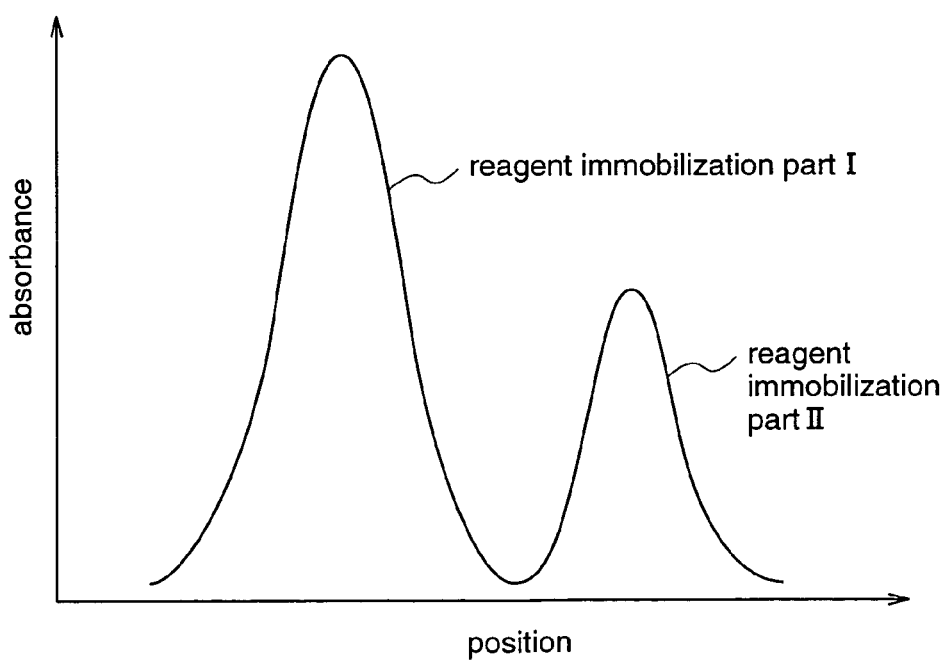
FIG. 3 is a diagram illustrating a measured waveform according to the first embodiment of the invention.

In the biosensor, about 50 μl of whole blood containing CRP is applied to the sample introduction part, and developed toward the absorption part to make an antigen-antibody reaction, thereby making a color reaction on the antibody immobilization part. The coloration status 5 minutes after the sample application to the biosensor was measured with a reflection absorbance measuring device. A result of measurement is shown in FIG. 2. FIG. 2 is a diagram for explaining measurement according to the second embodiment of the invention. In FIG. 2, reference numeral 11 denotes a light source, which is a 635 nm semiconductor laser. Further, a detection-side photoreceptor 12 is implemented by a photodiode. Furthermore, the biosensor 10 was scanned, and the amounts of the marker reagent bound onto the reagent immobilization parts I(S) and II(9) were obtained as absorbances by arithmetically processing the reflected and scattered light from the developing layer. The result of measurement is shown in FIG. 3. FIG. 3 is a diagram illustrating a measured waveform according to the second embodiment of the present invention. The waveform as shown in FIG. 3 is obtained when two reagent immobilization parts are provided, an antibody having a higher affinity is used for the upper-stream side with respect to the developing part onto which the sample solution is dropped, and the antigen concentration is constant. In this case, the light source and the photoreceptor were fixed, and the sensor was scanned. From the waveform thus obtained, a peak value (reflection absorbance) was read. In order to obtain such waveform, the light source side may be operated.

Figure 4:
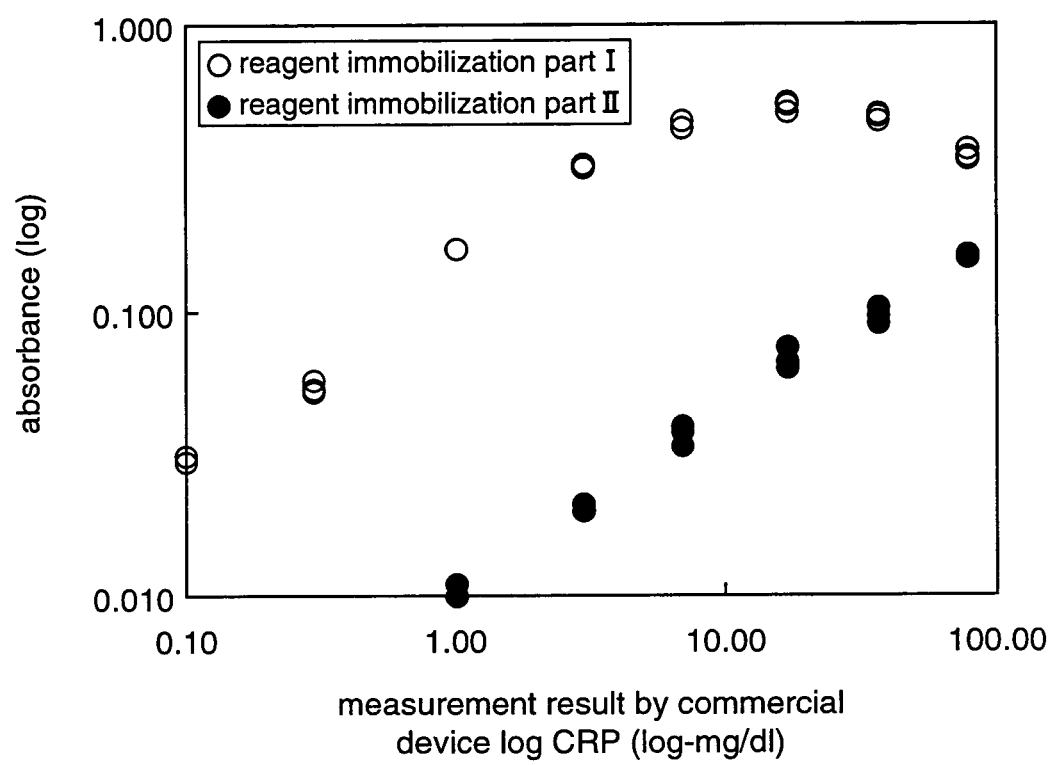
FIG. 4 is a diagram illustrating multi-concentration measurement results according to the first embodiment of the invention.

Next, whole bloods containing CRP having serum concentrations of 0.1 mg/dl, 0.3 mg/dl, 1.0 mg/dl, 3.0 mg/dl, 7.0 mg/dl, 17.0 mg/dl, 37.0 mg/dl, and 80 mg/dl are dropped to the biosensor and developed. The coloration states of the reagent immobilization part on the biosensor with respect to the bloods of the respective CRP concentrations were measured with a reflection absorbance measuring device. The absorbances at 635 nm were measured and plotted according to the respective CRP concentrations. The result is shown in FIG. 4. FIG. 4 is a diagram illustrating the result of multi-concentration measurement according to the second embodiment of the present invention. In FIG. 4, the abscissa shows the CRP concentration measured by a commercially available measurement device, with the sample solution used for the measurement being pipetted previously. Here, a reagent and a device based on a latex immunocoagulation method were employed. The ordinate shows the obtained absorbances. The white plots show the absorbances obtained from the reagent immobilization part I(5), and the black plots show the absorbances obtained from the reagent immobilization part II(9). It can be seen from FIG. 4 that the both have different responses to the CRP. Next, the measurement result will be described with reference to FIGS. 5(a) and 5(b). FIG. 5(a) is a schematic diagram illustrating a measurement dynamic range according to the first embodiment of the present invention, and FIG. 5(b) is a schematic diagram illustrating prozone judgement according to the first embodiment of the present invention. FIG. 5(a) is a schematic diagram of the result shown in FIG. 4. With reference to FIG. 5(a), since the reagent immobilization part I and the reagent immobilization part II have different CRP responses, these parts have different measurement ranges for CRP in the sample solution. That is, the area dynamic range 1 where the absorbance increases according to the CRP is the measurement area in the reagent immobilization part I, and the dynamic range 2 is the CRP measurement area in the reagent immobilization part 2. By using the results obtained from the reagent immobilization part 1 and the reagent immobilization part 2, the measurement dynamic range of the dynamic range 3 can be realized. For example, when the absorbance A1 or A4 is obtained in the reagent immobilization part I, if the absorbance in the reagent immobilization part II indicates B1, it is the CRP concentration at A1; on the other hand, if the absorbance in the reagent immobilization part II indicates B4, it is the CRP concentration at A4. In this way, measurement over a wide dynamic range can be realized in one test specimen by one-time measurement. Next, detection of prozone phenomenon will be described with reference to FIG. 5(b). FIG. 5(b) schematically shows the measurement result shown in FIG. 4, like FIG. 5(a). With reference to FIG. 5(b), since the reagent immobilization part I and the reagent immobilization part II show different CRP responses, these parts have different measurement ranges for CRP in the sample solution. A prozone phenomenon is detected utilizing this nature. In FIG. 5(b), B-point shown by a black triangle plot indicates a prozone judgement threshold value in the immunochromatography test specimen. The prozone judgement threshold value will be described as follows. For example, when the absorbance in the reagent immobilization part I is A1 or A4, the absorbance in the reagent immobilization part II is B1 for A1, and this is lower than the prozone judgement threshold value. In this case, by substituting this value into the calibration curve in the reagent immobilization part I, it is known that the CRP concentration of the sample solution is A1. However, when the absorbance in the reagent immobilization part II is B4, the CRP concentration is higher than the B-point. Therefore, this value judged as being outside the calibration curve of the reagent immobilization part I. In this way, judgement as to whether the reagent immobilization part is in the prozone area or not is realized on the basis of whether the CRP concentration is higher than a predetermined threshold value or not. The calibration curve described above is an area where the absorbance increases with an increase in the CRP concentration, and it is a mathematical expression that is previously derived from a sample solution whose concentration is known, and thereafter, used for calculating the CRP concentration of an unknown sample solution from the obtained absorbance.

(Quantitative Analysis 2 of Whole Blood CRP)

An immunochromatography test specimen including a reagent immobilization part I obtained by immobilizing an anti-CRP antibody D on a nitrocellulose film, reagent immobilization parts II and III obtained by immobilizing an anti-CRP antibody E on the nitrocellulose film, and a marker reagent which holds complexes of anti-CRP antibody F and gold colloid, is manufactured. This immunochromatography test specimen is shown in FIG. 6. In FIG. 6, the immunochromatography test specimen includes reagent immobilization parts I(5), II(9), and III(14) on which antibodies are immobilized, a marker reagent 4 as an area containing complexes of anti-CRP antibody F and gold colloid, which is closer to a developing start point onto which a sample solution is dropped than the reagent immobilization parts, and a sample solution introduction part 1. This immunochromatography test specimen is manufactured as follows.

a) Preparation for Immunochromatography Test Specimen

An anti-CRP antibody D solution which was diluted with a phosphate buffer solution to control the concentration was prepared. This antibody solution was applied on a nitrocellulose film by using a solution discharge device. Thereby, an antibody immobilization line I as a reagent immobilization part is obtained on the nitrocellulose film. Next, an anti-CRP antibody E having an affinity lower than that of the antibody used for the antibody immobilization line I was applied to a part 2 mm apart downstream from the sample solution introduction part, and a part further 2 mm apart from that part, whereby a reagent immobilization line II and a reagent immobilization line III were obtained. After being dried, the nitrocellulose film was immersed in a Tris-HCl buffer solution containing 1% skim milk, and shaken gently for 30 minutes. 30 minutes later, the film was moved into a Tris-HCl buffer solution tank and shaken gently for 10 minutes, and thereafter, the film was shaken gently for another 10 minutes in another Tris-HCl buffer solution tank, thereby to wash the film. After being washed twice, the film was taken out of the solution tank, and dried at room temperature.

The gold colloid was prepared by adding a 1% citric acid solution to a 0.01 gold chloride acid solution that is refluxing at 100° C. After the reflux was continued for 30 minutes, the solution was cooled at room temperature. Then, the anti-CRP antibody C was added to the gold colloid solution that was adjusted to pH9 by a 0.2M potassium carbonate solution, and the solution was shaken for several minutes. Thereafter, a 10% BSA (bovine serum albumin) solution of pH9 was added to the solution by such an amount that the concentration finally became 1%, and the solution was stirred, thereby to prepare an antibody-gold colloid complex (marker antibody) as a material to be detected. The marker antibody solution was subjected to centrifugation at 4° C. and 20000 G for 50 minutes to isolate the marker antibody. Then, the isolated marker antibody was suspended in a wash and buffer solution (1% BSA·phosphate buffer solution) and then subjected to centrifugation under the above-mentioned condition, thereby to wash and isolate the marker antibody. The marker antibody was suspended in a wash and buffer solution, and filtered through a 0.8 μm filter. Thereafter, the obtained marker antibody solution was prepared to an amount one-tenth as much as the original gold colloid solution, and stored at 4° C. The gold colloid marker antibody solution was set in a solution discharge device, and applied to portions apart from the immobilization lines I, II, and III on the anti-CRP antibody D and anti-CRP antibody E immobilized dry film, so as to have a positional relationship of the marker antibody, the immobilization line I, the immobilization line II, and the immobilization line III in this order from the sample solution application start position, and thereafter, the film was dried by vacuum freeze-dry. Thereby, a reaction layer carrier having the marker reagent on the immobilization film is obtained.

Next, the reaction layer carrier having the prepared marker reagent is affixed to a substrate comprising 0.5 mm thick white PET, and the substrate was cut into 5.0 mm parts (specimens). After the cutting, a 100 μm thick transparent tape is wound around each specimen from the marker antibody holding part to the end part. Then, a space formation member formed by laminating 100 μm thick transparent PET was affixed onto a center portion of the beginning part around which no transparent tape is wound, thereby forming a space part (5.0 mm wide×12.0 mm long×0.5 mm high). A potassium chloride solution prepared to 1.5M was dropped onto the space formation member, and thereafter, the space formation member was immediately frozen by liquid nitrogen to be freeze-dried, thereby forming the space formation member having the contraction agent holding part where potassium chloride is held in the dry state. Thus, the immunochromatography test specimen was manufactured.

b) Preparation of Sample

Human blood to which EDTA·2K was added as an anticoagulant was prepared so as to have a hematocrit value of 45%. CRP solutions of known concentrations were added to this blood to prepare CRP containing bloods having various known concentrations.

c) Measurement of Degree of Coloration on Test Specimen

In the biosensor, about 50 μl of whole blood containing CRP is applied to the sample introduction part, and developed toward the absorption part to make an antigen-antibody reaction, thereby making a color reaction on the antibody immobilization part. The coloration status 5 minutes after the sample application to the biosensor was measured in like manner as described for the quantitative analysis 1 of whole blood CRP shown in FIG. 2. A result of measurement is shown in FIG. 7.

Figure 7:
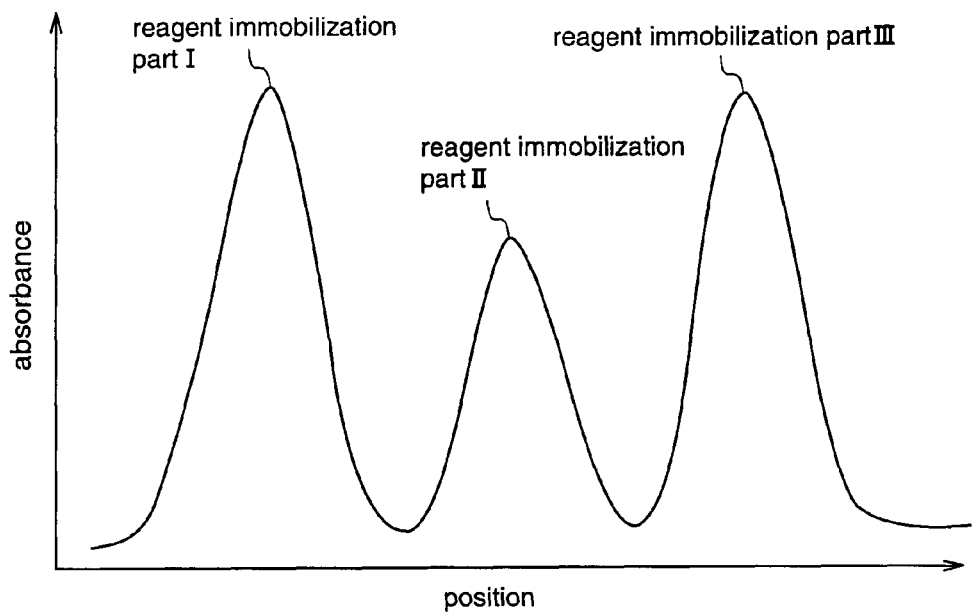
FIG. 7 is a diagram illustrating a measured waveform according to the second embodiment of the invention.

FIG. 7 is a diagram illustrating a measured waveform according to the second embodiment of the present invention. The waveform as shown in FIG. 7 is obtained when three reagent immobilization parts are provided, an antibody having a higher affinity is used for the upper-stream side with respect to the developing part onto which the sample solution is dropped, the same antibody is used for the reagent immobilization parts II and III, and the antigen concentration is constant. In this case, the light source and the photoreceptor were fixed, and the sensor was scanned. From the waveform thus obtained, a peak value (reflection absorbance) was read. In order to obtain such waveform, the light source side may be operated.

Figure 8:
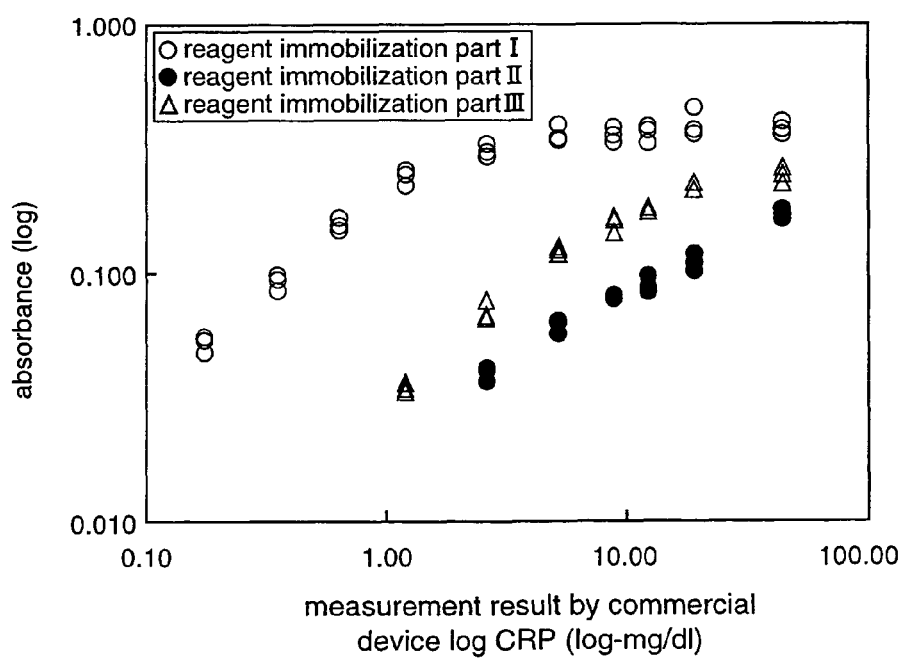
FIG. 8 is a diagram illustrating multi-concentration measurement results according to the second embodiment of the invention.

Next, whole bloods containing CRP having serum concentrations of 0.1 mg/dl, 0.3 mg/dl, 0.6 mg/dl, 1.0 mg/dl, 3.0 mg/dl, 6.0 mg/dl, 10.0 mg/dl, 15.0 mg/dl, 20.0 mg/dl, and 30 mg/dl are dropped to the biosensor and developed. The coloration states of the reagent immobilization part on the biosensor with respect to the bloods of the respective CRP concentrations were measured with a reflection absorbance measuring device. The absorbances at 635 nm were measured and plotted according to the respective CRP concentrations. The result is shown in FIG. 8. FIG. 8 is a diagram illustrating the result of multi-concentration measurement according to the second embodiment of the present invention. In FIG. 8, the abscissa shows the CRP concentration measured by a commercially available measurement device, with the sample solution used for the measurement being pipetted previously. Here, a reagent and a device based on a latex immunocoagulation method were employed. The ordinate shows the obtained absorbances. The white circle plots show the absorbances obtained from the reagent immobilization part I(5), the black circle plots show the absorbances obtained from the reagent immobilization part II(9), and the white triangle plots show the absorbances obtained from the reagent immobilization part III(14). It can be seen from FIG. 8 that the respective reagent immobilization parts have different responses to the CRP. Next, the measurement result will be described with reference to FIG. 9.

Figure 9:
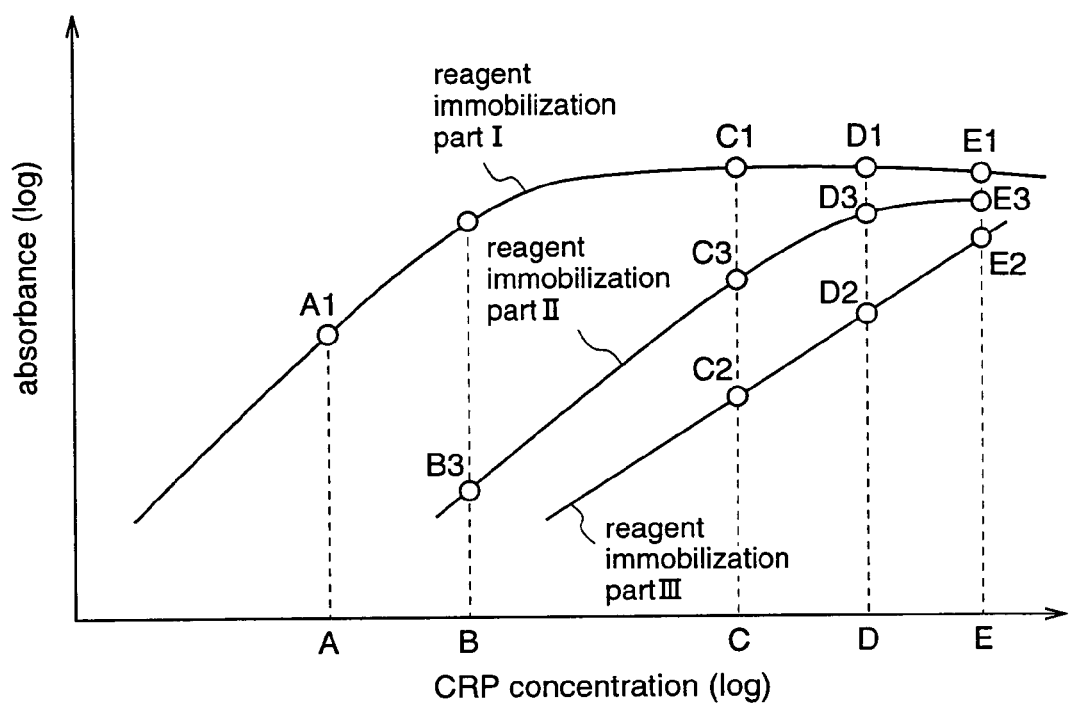
FIG. 9 is a schematic diagram illustrating a measurement result according to the second embodiment of the invention.

FIG. 9 is a schematic diagram illustrating the result of measurement according to the second embodiment of the present invention, i.e., the result shown in FIG. 8. With reference to FIG. 9, since the reagent immobilization part I and the reagent immobilization part II (the reagent immobilization part III) show different CRP responses, these parts have different measurement ranges for CRP in the sample solution. Further, even the reagent immobilization parts II and III having the same affinity show different responses to CRP. In FIG. 9, when the CRP concentration is A, a signal can be obtained only in the reagent immobilization part I (A1). In this case, CRP measurement can be executed using the reagent immobilization part I. When the CRP concentration is B, signals are obtained from the reagent immobilization part I(B1) and the reagent immobilization part III(B3). In this concentration range, however, no signal is obtained from the reagent immobilization part II. Therefore, it is known from these relationships that the signal obtained from the reagent immobilization part I is not a prozone area in the reagent immobilization part I but a linearly regressive area. Next, when the CRP concentration is C, D, or E, signals are obtained from all of the three reagent immobilization parts C1~C3, D1~D3, or E1~E3, respectively. In this case, it is known that the reagent immobilization part I (C1,D1,E1) is already in the prozone area, from that there are signals from the reagent immobilization part II (C2,D2,E2) and the reagent immobilization parts III (C3,D3,E3). Next, a description will be given of the CRP concentration C, CRP concentration D, and CRP concentration E. At the CRP concentration C, signals are obtained from all of the three parts, and there is a sufficient difference between the signal from the reagent immobilization part II(C2) and the signal from the reagent immobilization part III(C3). In this case, the CRP concentration can be calculated using the reagent immobilization part III. The signals from the reagent immobilization part II(D2,E2) and the reagent immobilization part III(D3,E3) at the CRP concentration D and CRP concentration E approach each other from the CRP concentration D to the CRP concentration E. From the relationship of these approaching parts, when it is desired to use the measurement dynamic range widely, the reagent immobilization part III can be used for obtaining the CRP concentration up to the point C, and the reagent immobilization part II can be used for obtaining the CRP concentration exceeding the point C. Although this appears to be possible only from the signal in the reagent immobilization part II, when a very-high concentration anti-CRP that is not shown in FIG. 9 is used, it might be lowered to a similar signal. It is possible to precisely judge whether a measurable area (a part that linearly changes according to the CRP concentration in FIG. 9) or an antigen excess area. Further, when the CRP concentration is E or higher, since all signals are very close to each other, it can be judged as a prozone area in this measurement system. Since three reagent immobilization parts are provided and two kinds of reagents for immobilization are used, measurement of a sample solution in which the concentration of an analyte is unknown can be incredibly carried out in a wider measurement dynamic range by using a single biosensor, and moreover, accurate measurement can be realized by the prozone detection and the like. While in this second example reagent immobilization parts are provided in three positions, it is needless to say that more reagent immobilization parts may be provided by the user, or the relationships among the respective reagent immobilization parts may be changed according to the affinities of the antibodies to be employed. The signals described above are signals from the marker reagent bound to the reagent immobilization parts, and these signals can be visually observed as desired. However, for more accurate measurement, it is preferable to use a detector as described in this example.

As a biodevice according to the embodiments of the present invention, a biosensor comprising a chromatography material made of an arbitrary porous carrier, such as nitrocellulose or glass fiber filter, is employed. The biosensor made of such material has the function of analytically detecting a specific material by using an arbitrary principle of measurement such as an antigen-antibody reaction to qualitatively or quantitatively analyze the material.

Further, while in this example a biosensor in which a marker reagent and a reagent immobilization part are provided on the same nitrocellulose film is employed, a marker reagent which is supported by a porous carrier different from nitrocellulose, such as a nonwoven fabric, may be put on a support member. While gold colloid is used as a marker constituting the marker reagent, any material may be used so long as it produces some change before and after the reaction, for example, a coloring material, fluorescent material, phosphorescent material, light-emitting material, oxidation-reduction material, enzyme, nucleic acid, or endoplasmic reticulum may be employed.

Furthermore, while in this example one marker reagent part and plural reagent immobilization parts are employed, the market reagent part is not necessarily provided in one position, and the biosensor may be constituted by combination of plural reagent immobilization parts and plural reagents. For example, the biosensor may be constituted such that a marker reagent is provided at the upper-stream side of each reagent immobilization part of plural reagent immobilization parts. In this case, although the construction technique in manufacturing is complicated, an arbitrary number of marker reagents can be provided in arbitrary positions.

As examples of sample solutions to be measured, there are water, aqueous solution, bodily fluid such as urine, blood, blood plasma, blood serum, or saliva, solution in which a solid, powder, or gas is dissolved, and the like. As examples of applications for these sample solutions, there are urinalysis, pregnancy test, water examination, fecal examination, soil analysis, food analysis, and the like. Further, while in this second embodiment C-reactive protein (CRP) is taken as an example of the analyte, the analyte may be antibody, immunoglobulin, hormone, protein and protein derivative such as enzyme and peptide, bacterium, virus, eumycetes, mycoplasma, parasite and an infectious material such as a product or a component of parasite, chemical drug such as curative medicine and abused drug, or tumor marker. To be specific, the analyte may be, for example, human chrionic gonadotropin (hCG), luteinizing hormone (LH), thyroid-stimulating hormone, follicular hormone, parathyroid hormone, adrenocorticotropic hormone, estradiol, prostate specific antigen, hepatitis B surface antigen, myoglobin, CRP, cardiac troponin, HbA1c, albumin, or the like. Further, applications for these analytes include environmental analysis such as water examination and soil analysis, food analysis, and the like. According to the embodiments described above, simple, speedy, highly sensitive and efficient measurement with high precision that enables detection of prozone areas can be realized. Further, simple, speedy, highly sensitive and efficient measurement having a sufficiently wide dynamic range for analyte concentration in onetime measurement can be realized.

APPLICABILITY IN INDUSTRY

A biosensor using immunochromatography and a measurement method using the biosensor according to the present invention can be utilized for performing simple, precise, and speedy measurement in various fields including not only medical diagnosis scenes such as clinical fields but also food hygiene fields, environmental measurement fields, and the like.

The invention claimed is:

1. A biosensor comprising a developing layer for developing a sample solution containing an analyte, said developing layer comprising:
  a plurality of reagent immobilization parts, each part having one reagent immobilized thereto;
  a marker reagent part on which a marker reagent is held in its dry state, and the marker reagent is dissolvable by developing the sample solution;
  a sample solution applying part to which the sample solution is applied, and
  the biosensor having a fine space which is formed by a space formation member comprising a liquid impermeable material and covers the entirety of an end portion of the developing layer in the sample solution applying part;
  wherein
  said fine space which has a cell component contraction reagent and is connected to said developing layer and is a space into which a predetermined volume of the sample solution flows by capillary phenomenon to be mixed with the cell component contraction reagent when the sample solution is in contact with said fine space,
  the reagents on each part of the reagent immobilization parts are different from each other, and have different affinities for the analyte in the sample solution, and
  the sample solution, when it moves on the developing layer, comes in contact with the respective parts included in the developing layer, successively, in order of the sample solution applying part, the marker reagent part, and the plural reagent immobilization parts.

2. The biosensor as defined in Claim 1, wherein the reagents immobilized to the plural reagent immobilization parts are antibodies, the analyte in the sample solution is an antigen, a first antibody having a higher affinity for the analyte in the sample solution is immobilized on a first reagent immobilization part, and a second antibody with an affinity for the analyte in the sample solution which is lower than that of the first antibody is immobilized on a second reagent immobilization part, wherein the first reagent immobilization part is upstream of the second reagent immobilization part in the sample solution developing direction.

3. The biosensor as defined in Claim 1, wherein the reagents in the plural reagent immobilization parts are monoclonal antibodies.

4. The biosensor as defined in Claim 1, wherein the reagents on the plural reagent immobilization parts have different affinities for the same analyte in the sample solution, whereby the reagents have different dynamic ranges for measuring the concentration of the analyte in the sample solution.

5. The biosensor as defined in Claim 1, wherein the reagents in the plural reagent immobilization parts recognize the same epitope.

6. The biosensor as defined in Claim 1, wherein the plural reagent immobilization parts are provided at two positions on the developing layer.

7. The biosensor as defined in Claim 1, wherein the plural reagent immobilization parts themselves are physically adjacent to each other.

8. The biosensor as defined in Claim 1, wherein the developing layer employs a lateral flow system, wherein the reagents of the plural reagent immobilization parts are immobilized in the shape of lines along a direction perpendicular to the sample solution developing direction to form the plural reagent immobilization parts, the lines having a line width of 0.5 mm-2.0 mm, and the lines of the plural reagent immobilization parts being separated by an interval of 1.0 mm or longer.

9. The biosensor as defined in Claim 1, wherein all of the reagents including the marker reagent and the immobilized reagents are in their dry states.

10. The biosensor as defined in Claim 1, wherein the sample solution is urine, saliva, or blood.

11. The biosensor as defined in Claim 1, which is an immunochromatograph.

12. A measurement method employing the biosensor as defined in Claim 1, which comprises contacting the sample solution applying part of the biosensor with a sample solution containing an analyte, and measuring the amounts of the marker reagent bound to the plural reagent immobilization parts, thereby to qualitatively or quantitatively analyze the analyte in the sample solution.

13. The measurement method as defined in Claim 12, wherein the method for measuring the amounts of the marker reagent bound to the plural reagent immobilization parts employs an electromagnetic wave.

14. The measurement method as defined in Claim 13, wherein the method for measuring the amounts of the marker reagent bound to the plural reagent immobilization parts comprises measuring a diffused electromagnetic wave obtained when an electromagnetic wave is reflected off the biosensor.

15. The measurement method as defined in Claim 13, wherein an electromagnetic wave source used for the measurement is scanned with respect to the biosensor, or the biosensor is scanned with respect to the electromagnetic wave source, thereby to measure the amounts of the marker reagent bound to the reagent immobilization parts.

16. The measurement method as defined in Claim 12, wherein the measurement results of the amounts of the marker reagent bound to the plural reagent immobilization parts are compared with respective threshold values, thereby to perform prozone judgement.

17. The measurement method as defined in Claim 12, wherein
  the amount of the marker reagent bound to the reagent immobilization part which is positioned on the uppermost stream side with respect to the sample solution applying part is first measured, and the amounts of the marker reagent bound to the other reagent immobilization parts are then simultaneously measured; and
  the measured value of the amount of the marker reagent bound to the uppermost stream side reagent immobilization part is subjected to prozone judgement by comparing the measured value to the measured values of the amounts of marker reagent bound to the other reagent immobilization parts with a threshold value.

18. The measurement method as defined in Claim 12, wherein the measurement is one-step immunochromatography which is started by the sample solution applying operation.

19. The biosensor as defined in Claim 1, wherein the reagent immobilization parts are provided at three positions.

20. The biosensor as defined in Claim 19, wherein the reagents immobilized to the plural reagent immobilization parts are antibodies, and a first antibody having the highest affinity for the analyte in the sample solution is immobilized on the first reagent immobilization part, and a second and a third antibody having an affinity for the analyte in the sample solution which is lower than that of the first antibody are immobilized in the second and third reagent immobilization parts, wherein the first reagent immobilization part is upstream of the second and third reagent immobilization parts in the sample solution developing direction.

21. The measurement method as defined in Claim 12, wherein the reagent immobilization parts are provided in three positions.

22. The measurement method employing the biosensor as defined in Claim 20, wherein the amounts of the marker reagent bound to the plural reagent immobilization parts are measured, thereby to qualitatively or quantitatively analyze the analyte in the sample solution.

* * * * *